United States Patent
Veselovska et al.

(10) Patent No.: US 11,299,510 B2
(45) Date of Patent: Apr. 12, 2022

(54) SUBSTITUTED PYRIDOPYRROLOPYRIMIDINE RIBONUCLEOSIDES FOR THERAPEUTIC USES

(71) Applicants: USTAV ORGANICKE CHEMIE A BIOCHEMIE AV CR, V.V.I., Prague (CZ); UNIVERZITA PALACKEHO V OLOMOUCI, Olomouc (CZ)

(72) Inventors: Lucia Veselovska, Liptovska Luzna (SK); Michal Hocek, Prague (CZ); Marian Hajduch, Moravsky Beroun (CZ); Petr Dzubak, Brodek u Prerova (CZ)

(73) Assignees: USTAV ORGANICKE CHEMIE A BIOCHEMIE AV CR, V.V.I., Prague (CZ); UNIVERZITA PALACKEHO V OLOMOUCI, Olomouc (CZ)

( * ) Notice: Subject to any disclaimer, the term of this patent is extended or adjusted under 35 U.S.C. 154(b) by 0 days.

(21) Appl. No.: 16/978,093

(22) PCT Filed: Mar. 4, 2019

(86) PCT No.: PCT/CZ2019/050008
§ 371 (c)(1),
(2) Date: Sep. 3, 2020

(87) PCT Pub. No.: WO2019/174657
PCT Pub. Date: Sep. 19, 2019

(65) Prior Publication Data
US 2021/0002321 A1    Jan. 7, 2021

(30) Foreign Application Priority Data
Mar. 12, 2018 (CZ) .............................. CZ2018-121

(51) Int. Cl.
*C07H 19/23*  (2006.01)
*A61P 35/04*  (2006.01)

(52) U.S. Cl.
CPC .............. *C07H 19/23* (2013.01); *A61P 35/04* (2018.01)

(58) Field of Classification Search
None
See application file for complete search history.

(56) References Cited

FOREIGN PATENT DOCUMENTS

| WO | 2009089804 A1 | 7/2009 |
|---|---|---|
| WO | 2010121576 A2 | 10/2010 |
| WO | 2018001383 A1 | 1/2018 |
| WO | 2018001393 A1 | 1/2018 |
| WO | 2018024265 A1 | 2/2018 |

OTHER PUBLICATIONS

Tichy et al., Bioorganic and Medicinal Chemistry—vol. 21, 17, 2013, pp. 5362-5372. (Year: 2013).*
Chung, Fung-Lung, Synthesis of certain [6:5:6] linear tricyclic nucleosides as potential ant itumor agents11 , Journal of Medicinal Chemistry, American Chemical Society, us. vol. 23, No. 11, Nov. 1, 1980 (Nov. 1, 1980), pp. 1158-1166, XP002977960, ISSN: 0022-2623, DOI: 10.1021/JM00185A002, first page downloaded Sep. 2, 2020.
Tichy, Michal et al: "Synthesis and biological activity of benzo-fused 7-deazaadenosine analogues. 5- and6-substituted 4-amino-or4-alkylpyrimido[4,5-b]indole ribonucleosides", Bioorganic & Medicinal Chemistry,vol. 21, No. 17, Jan. 17, 2013 (Jan. 17, 2013), pp. 5362-5372, XP028690133,ISSN: 0968-0896, DOI:10.1016/J.BMC.2013.06.011.
Tichy, Michal et al: "Synthesis and antiviral activity of 4,6-disubstituted pyrimido[4,5-b]indole ribonucleosides", Bioorganic & Medicinal Chemistry, vol. 20, No. 20, Aug. 24, 2012 (Aug. 24, 2012), pp. 6123-6133, XP028943300, ISSN: 0968-0896, DOI: 10.1016/J.BMC.2012.08.021.
International Search Report and Written Opinion for corresponding PCT application No. PCT/CZ2019/050008, dated Apr. 25, 2019.

* cited by examiner

*Primary Examiner* — Traviss C Mcintosh, III
(74) *Attorney, Agent, or Firm* — Notaro, Michalos & Zaccaria P.C.

(57) ABSTRACT

Substituted pyridopyrrolopyrimidine ribonucleosides of general formula I, wherein R is as described in the independent claim, preferably R is selected from the group comprising thiophen-3-yl, furan-2-yl, furan-3-yl, benzofuran-2-yl, methylsulfanyl, methoxy, amino, dimethylamino, methyl; and pharmaceutically acceptable salt thereof, their optical isomers and mixtures of such optical isomers. Compounds according to the invention show strong cytostatic and cytotoxic effects on cell lines of tumor origin in a wide variety of diseases including tumors of different histogenetic origin.

11 Claims, No Drawings

SUBSTITUTED PYRIDOPYRROLOPYRIMIDINE RIBONUCLEOSIDES FOR THERAPEUTIC USES

FIELD OF THE INVENTION

The invention provides a new type of compounds with anti-cancer activity and their therapeutic use.

BACKGROUND OF THE INVENTION

Although dozens of antiproliferative drugs already exist, the treatment of many types of leukemia and tumors still has a low success rate. Thus the development of new type of compounds with anti-cancer properties is necessary.

Recently our group discovered, patented and published several new classes of cytostatic compounds, 7-(het)aryl-7-deazaadenosines {formula A, ref.: Bourderioux, A.; Nauš, P.; Hocek, M., U.S. 61/171,656 (2009), PCT/CZ2010/000050, WO2010121576 A2; Bourderioux, A.; Nauš, P.; Perlíková, P.; Pohl, R.; Pichová, I.; Votruba, I.; Džubák, P.; Konečný, P.; Hajdúch, M.; Stray, K. M.; Wang, T.; Ray, A. S.; Feng, J. Y.; Birkus, G.; Cihlar, T.; Hocek, M. Synthesis and significant cytostatic activity of 7-hetaryl-7-deazaadenosines. J. Med. Chem. 2011, 54, 5498-55071}, or 6-hetaryl-7-deazapurine ribonucleosides bearing hydrogen or fluorine in position 7 {formula B, Hocek, M.; Nauš, P., PCT/CZ2009/000004; Nauš, P.; Pohl, R; Votruba, I.; Džubák, P.; Hajdúch, M; Ameral, R.; Birkuš, G.; Wang, T.; Ray, A. S.; Mackman, R.; Cihlar, T.; Hocek, M. 6-(Het)aryl-7-Deazapurine Ribonucleosides as Novel Potent Cytostatic Agents. J. Med. Chem. 2010, 53, 460-4701}. These compounds exhibited nanomolar cytotoxic and cytostatic effect against a broad spectrum of solid and leukemia tumors.

Pyrimidoindole ribonucleosides prepared in our group are the only known type of annulated deazapurine nucleosides, however, they displayed only minor or no cytotoxicity {formula C, ref.: Tichý, M.; Pohl, R.; Xu, H. Y.; Chen, Y.-L.; Yokokawa, F.; Shi, P.-Y.; Hocek, M. Synthesis and antiviral activity of 4,6-disubstituted pyrimido[4,5-b]indole ribonucleosides. Bioorg. Med. Chem. 2012, 20, 6123-6133; Tichý, M.; Pohl, R.; Tlouštová, E.; Weber, J.; Bahador, G.; Lee, Y.-J.; Hocek, M. Synthesis and biological activity of benzo-fused 7-deazaadenosine analogues. 5- and 6-substituted 4-amino- or 4-alkylpyrimido [4,5-b]indole ribonucleosides. Bioorg. Med. Chem. 2013, 21, 5362-53721}. Subsequently prepared 4-substituted hetero-cyclopentadiene-pyrrolopyrimidine ribonucleosides, specifically thienopyrrolo[2, 3-d]pyrimidines {formula E, ref.: WO 2018001383; Tichý, M.; Smoleń, S.; Tloušt'ová, E.; Pohl, R.; Oždian, T.; Hejtmánková, K.; Lišková, B.; Gurská, S.; Džubák, P.; Hajdúch, M.; Hocek, M. Synthesis and cytostatic and antiviral profiling of thieno-fused 7-deazapurine ribonucleosides J. Med. Chem. 2017, 60, 2411-2424}, pyrrolo- and furo-fused 7-deazapurine ribonucleosides {formula D, ref.: Tokarenko, A.; Lišková, B.; Smoleń, S.; Táborská, N.; Tichý, M.; Gurská, S.; Perlíková, P.; Frydrych, I.; Tloušt'ová, E.; Znojek, P.; Mertlíková-Kaiserová, H.; Poštová Slavětínská, L.; Pohl, R.; Klepetářová, B.; Khalid, N.; Wenren, Y.; Laposa, R. R.; Džubák, P.; Hajdúch, M.; Hocek, M.: "Synthesis and cytotoxic and antiviral profiling of pyrrolo- and furo-fused 7-deazapurine ribonucleosides J. Med. Chem. 2018, 61, 9347-9359} showed strong cytostatic and cytotoxic effects on cell lines of preferentially tumor origin and a wide variety of diseases including tumors of different histogenic origin.

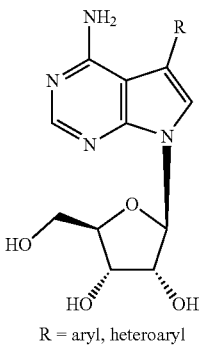

(A)

R = aryl, heteroaryl

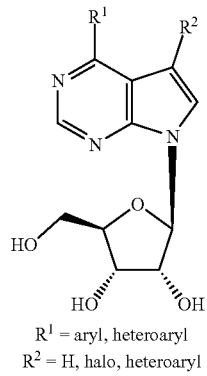

(B)

$R^1$ = aryl, heteroaryl
$R^2$ = H, halo, heteroaryl

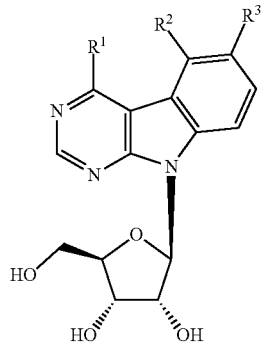

(C)

$R^1$ = NH$_2$, Me, MeNH$_2$, Me$_2$NH, cyclopropyl, heteroaryl, aryl
$R^2$ = H, Cl, heteroaryl
$R^3$ = H, Cl, heteroaryl

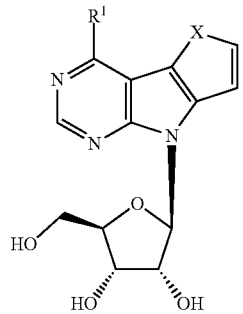

(D)

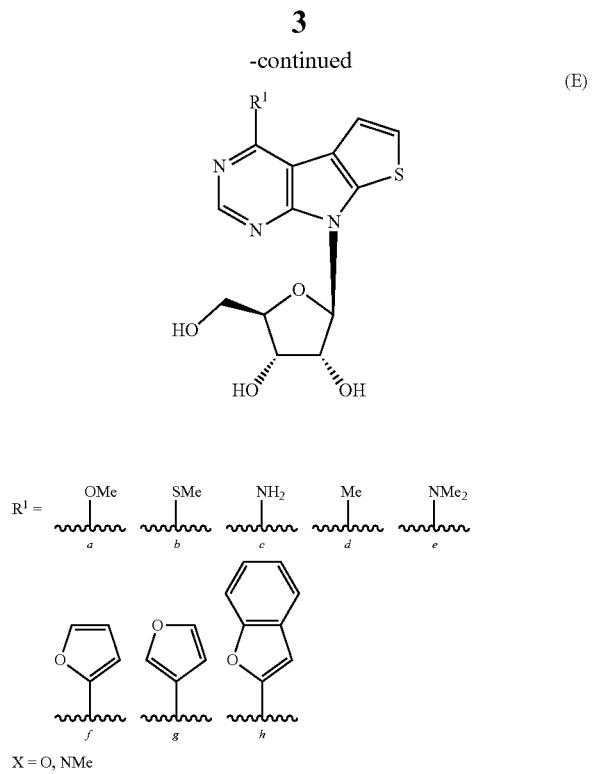

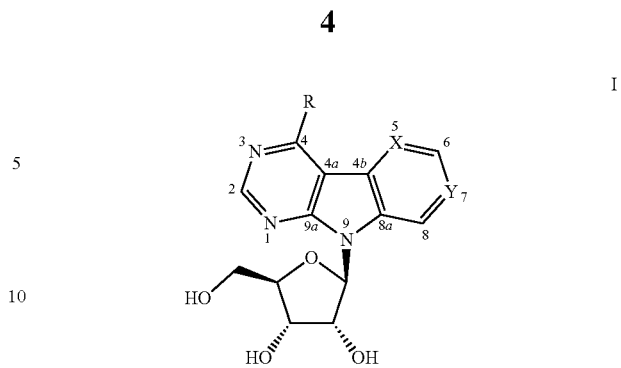

SUMMARY OF THE INVENTION

This invention describes new 4-substituted pyridopyrrolopyrimidine ribonucleosides possessing pyridine nitrogen in positions 5 or 7, exhibiting strong cytostatic and cytotoxic effects on cell lines preferentially of tumor origin and on broad spectrum of cancers of various histogenetic origin.

The presence of fused six-membered pyridine ring at positions 7 and 8 of deazapurine system makes these compounds significantly different from all types of previously synthesized 7-deazapurine derivatives of general formulas A and B, pyrimidoindole ribonucleosides of formula C and also of the hetero-cyclopentadiene-pyrrolopyrimidine ribonucleosides of general formula D and E.

As pyridopyrrolopyrimidine ribonucleosides themselves are new undescribed compounds unknown in nature, their biological activity has not been studied. Pyridopyrrolopyrimidine ribonucleosides represent a new and unique type of nucleosides with rigid tricyclic base, which leads to new type of interaction with biological system and therefore to different mechanism of action than all the other 7-substituted 7-deazapurine nucleosides. The preliminary results showed that the presence of nitrogen atom at one of the two specific ring positions is crucial for cytostatic and cytotoxic effect. Only pyridopyrrolopyrimidine ribonucleosides possessing nitrogen at the position 5 or 7 on the pyridine ring showed significant submicromolar in vitro cytotoxic activity, whilst pyridopyrrolopyrimidine ribonucleosides possessing nitrogen at the position 6 and 8 were not active at all. Moreover, the compounds with R=NH$_2$ had a particularly high activity, which makes this class of compounds different from other heteroaryl-fused 7-deazapurine nucleoside classes.

This invention provides substituted pyridopyrrolopyrimidine ribonucleosides of general formula I:

wherein,
X is a nitrogen atom and Y is a carbon atom; or
X is a carbon atom and Y is a nitrogen atom;
and wherein
R is selected from the group comprising
C1-C5 alkyl, optionally substituted by at least one substitutent selected from hydroxy, sulfanyl, amino, C1-C5 alkoxy, C1-C5 sulfanyl, C1-C5 alkylamino, di(C1-C5 alkyl)amino;
C2-C6 alkenyl, optionally substituted by at least one substitutent selected from hydroxy, sulfanyl, amino, C1-C5 alkoxy, C1-C5 sulfanyl, C1-C5 alkylamino, di(C1-C5 alkyl)amino;
C6-C12 aryl, optionally substituted by at least one substitutent selected from C1-C5 alkyl, hydroxy, sulfanyl, amino, C1-C5 alkoxy, C1-C5 sulfanyl, C1-C5 alkylamino, di(C1-C5 alkyl)amino;
C4-C12 heteroaryl, comprising at least one heteroatom selected from O and S; optionally substituted by at least one substituent selected from C1-C5 alkyl, hydroxy, sulfanyl, amino, C1-C5 alkoxy, C1-C5 sulfanyl, C1-C5 alkylamino, di(C1-C5 alkyl)amino;
amino,
C1-C5 alkylamino,
di(C1-C5 alkyl)amino,
C1-C5 alkoxy,
C1-C5 alkylsulfanyl,
and pharmaceutically acceptable salt thereof.

When compounds of formula I are optically active, formula I shall be understood as including individual optical isomers and mixtures of optical isomers, including racemic mixtures.

In one preferred embodiment, R is selected from the group comprising amino, C1-C5 alkyl, phenyl, naphthyl, furan-2-yl, furan-3-yl, thiophen-3-yl, thiophen-2-yl, benzofuryl, C1-C5 alkylsulfanyl, C1-C5 alkylamino, di(C1-C5 alkyl)amino, C1-C5 alkoxy.

More preferably, R is selected from the group comprising amino, thiophen-3-yl, furan-2-yl, furan-3-yl, benzofuran-2-yl, methylsulfanyl, methoxy, dimethylamino, methyl or chloro.

As described herein and unless otherwise indicated, the individual substituents have the following meanings:
alkyl is a linear or branched hydrocarbon chain containing the number of carbons indicated at each occurrence;
alkenyl means a straight or branched chain hydrocarbon chain containing one or more double bonds and containing the number of carbon atoms indicated at each occurrence;
aryl is a hydrocarbon chain comprising at least one aromatic ring and containing the number of carbons indicated at each occurrence. The aryl may also contain more than one aromatic ring, then these rings may be condensed or non-fused;

heteroaryl is a hydrocarbon group containing at least one heteroatom and at least one aromatic ring; the number of carbons and the number and type of heteroatom being indicated at each occurrence. Heteroaryl may also contain more than one aromatic ring, then these rings may be condensed or non-fused;

hydroxy denotes —OH;

sulfanyl denotes —SH;

amino denotes —NH$_2$;

alkylamino is a group formed by the substitution of one hydrogen atom of an amino group by the above-defined alkyl;

dialkylamino is a group formed by the substitution of two hydrogen atoms of an amino group by two alkyl groups defined above, which are the same or different;

alkoxy refers to a group —OR', wherein R' corresponds to the definition of alkyl;

alkylsulfanyl represents a group —SR', wherein R' corresponds to the definition of alkyl.

As used herein, the term "pharmaceutically acceptable salts" refers to salts that retain the biological effectiveness and properties of the compounds of this invention and which are not biologically or otherwise undesirable. In many cases, the compounds of the present invention are capable of forming acid and/or base salts by virtue of the presence of amino group or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in Remington's Pharmaceutical Sciences, 20th ed., Mack Publishing Company, Easton, Pa., (1985), which is herein incorporated by reference.

In a preferred embodiment, the present invention provides the following pyridopyrrolopyrimidine ribonucleosides of formula I:

4-(furan-3-yl)-9-(β-D-ribofuranosyl)-9H-pyrido[2',3':4,5]pyrrolo[2,3-d]pyrimidine 4-(furan-2-yl)-9-(β-D-ribofuranosyl)-9H-pyrido[2',3':4,5]pyrrolo[2,3-d]pyrimidine 4-(thiophen-3-yl)-9-(β-D-ribofuranosyl)-9H-pyrido[2',3':4,5]pyrrolo[2,3-d]pyrimidine 4-(benzofuran-2-yl)-9-(β-D-ribofuranosyl)-9H-pyrido[2',3':4,5]pyrrolo[2,3-d]pyrimidine 4-methyl-9-(β-D-ribofuranosyl)-9H-pyrido[2',3':4,5]pyrrolo[2,3-d]pyrimidine 4-(dimethylamino)-9-(β-D-ribofuranosyl)-9H-pyrido[2',3':4,5]pyrrolo[2,3-d]pyrimidine 4-amino-9-(β-D-ribofuranosyl)-9H-pyrido[2',3':4,5]pyrrolo[2,3-d]pyrimidine 4-methoxy-9-(β-D-ribofuranosyl)-9H-pyrido[2',3':4,5]pyrrolo[2,3-d]pyrimidine 4-(methylsulfanyl)-9-(β-D-ribofuranosyl)-9H-pyrido[2',3':4,5]pyrrolo[2,3-d]pyrimidine 4-(furan-3-yl)-9-(β-D-ribofuranosyl)-9H-pyrido[4',3':4,5]pyrrolo[2,3-d]pyrimidine 4-(furan-2-yl)-9-(β-D-ribofuranosyl)-9H-pyrido[4',3':4,5]pyrrolo[2,3-d]pyrimidine 4-(thiophen-3-yl)-9-(β-D-ribofuranosyl)-9H-pyrido[4',3':4,5]pyrrolo[2,3-d]pyrimidine 4-(benzofuran-2-yl)-9-(β-D-ribofuranosyl)-9H-pyrido[4',3':4,5]pyrrolo[2,3-d]pyrimidine 4-methyl-9-(β-D-ribofuranosyl)-9H-pyrido[4',3':4,5]pyrrolo[2,3-d]pyrimidine 4-(dimethylamino)-9-(β-D-ribofuranosyl)-9H-pyrido[4',3':4,5]pyrrolo[2,3-d]pyrimidine 4-amino-9-(β-D-ribofuranosyl)-9H-pyrido[4',3':4,5]pyrrolo[2,3-d]pyrimidine 4-methoxy-9-(β-D-ribofuranosyl)-9H-pyrido[4',3':4,5]pyrrolo[2,3-d]pyrimidine 4-(methylsulfanyl)-9-(β-D-ribofuranosyl)-9H-pyrido[4',3':4,5]pyrrolo[2,3-d]pyrimidine.

Additionally, the present invention provides compounds of formula I for use as a medicament.

The present invention provides substituted pyridopyrrolopyrimidine ribonucleosides of formula I for inhibition of pathological cell proliferation of tumor or non-tumor or cancer disease associated with cell hyperproliferation.

The present invention provides substituted pyridopyrrolopyrimidine ribonucleosides of formula I for use in a method of treatment of tumor or cancer diseases, covering e.g. epithelial, mesenchymal and neuroectoderm origin tumors.

The present invention provides substituted pyridopyrrolopyrimidine ribonucleosides of formula I for use in a method of treatment of non-tumor disease associated with cell hyperproliferation.

The present invention provides substituted pyridopyrrolopyrimidine ribonucleosides of formula I for the preparation of a medicament for treatment of tumor or cancer diseases, covering e.g. epithelial, mesenchymal and neuroectoderm origin tumors.

Preferably, the tumors and cancers are selected from hematopoietic cancers such as leukemias; lung cancers such as lung adenocarcinoma, colorectal cancer, osteosarcoma, cancers of breast, prostate, pancreas, gastrointestinal tract, kidney, liver, head and neck, brain.

The present invention provides a pharmaceutical composition comprising a therapeutically effective amount of a compound of formula I and one or more pharmaceutically acceptable excipients.

The invention also provides a method of treating a neoplastic disease or cellular proliferation disease in a subject comprising administering to the subject a therapeutically effective amount of a compound of formula I.

The term "therapeutically effective amount" of a compound of the present invention refers to an amount of the compound of the present invention that will elicit the biological or medical response of a subject, or ameliorate symptoms, slow or delay disease progression, or prevent a disease, etc. In a preferred embodiment, the "effective amount" refers to the amount that inhibits or reduces proliferation of cancer cells, or inhibiting or reducing tumor/cancer growth in vitro or in vivo, or inhibiting or reducing a neoplastic disease in a subject such as a mammal. In another preferred embodiment, it also refers to the amount that reduces the primary tumor/cancer size, inhibits cancer cell infiltration into peripheral organs, slows or stops tumor metastasis, or relieves at least to some extent one or more symptoms associated with tumor or cancer, etc.

As used herein, the term "subject" refers to an animal Preferably, the animal is a mammal. The term "subject" also refers to for example, primates (e.g., humans), cows, sheep, goats, horses, dogs, cats, rabbits, rats, mice, fish, birds and the like. In a preferred embodiment, the subject is a human. As used herein, the term "pharmaceutically acceptable excipient" includes any and all solvents, dispersion media, coatings, surfactants, antioxidants, preservatives (e.g., antibacterial agents, antifungal agents), isotonic agents, absorption delaying agents, salts, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except in so far as any conventional excipient is incompatible with the active ingredient, its use in the therapeutic or pharmaceutical compositions is contemplated.

The invention provides compounds of formula I for use in the form of active substance of a pharmacologically acceptable medium, which can be made by common procedures known in the field, e.g. active substance can be bound to or mixed with pharmaceutically acceptable inert (in)organic excipients.

The invention also provides compounds of formula I for use as a second active substance, which has synergistic effect with other active substances in known medicaments, or administration of compounds of formula I together with such medicaments.

In one embodiment, the present invention provides a compound of formula I as a prodrug or in other suitable form, which releases active compound in vivo.

DETAILED DESCRIPTION OF THE INVENTION

Compounds Numbering

Following numbering of compounds is used:

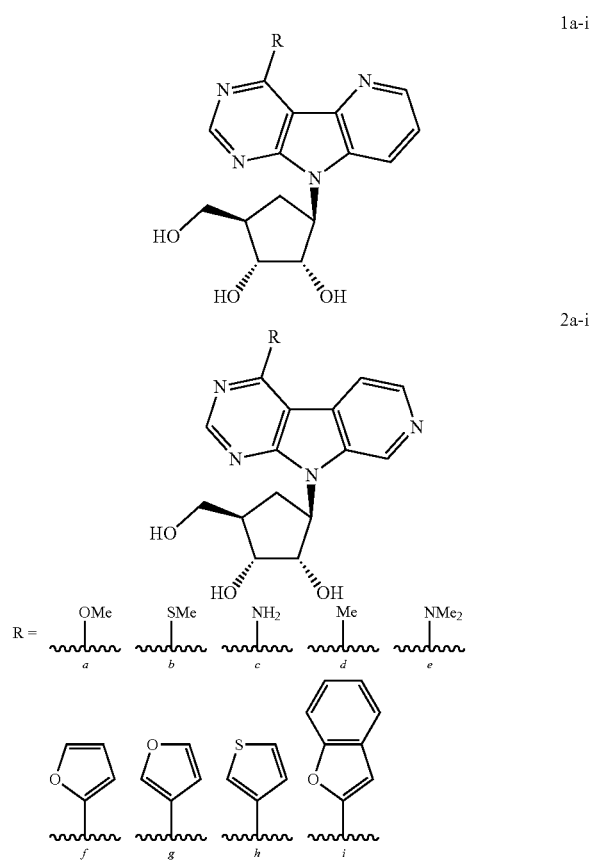

Synthesis of Compounds

Key-intermediate benzoylated 4-chloropyridopyrrolopyrimidine ribonucleosides possessing pyridine nitrogen in different positions were synthesised by 5-step procedure starting from corresponding chloronitropyridines 3 and 4. The synthesis employs key nucleophilic substitution of chlorine atom with ethyl cyanoacetate (Finch, N.; Robinson, M. M.; Valerio, M. P. A Synthesis of 4-Azaoxindole J. Org. Chem. 1972, 37, 51-53). The compounds thus prepared were then reduced by zinc dust, followed by cyclisation using formamide (Reader, J. C.; Matthews, T. P.; Klair, S.; Cheung, K. M.; Scanlon, J.; Proisy, N.; Addison, G.; Ellard, J.; Piton, N.; Taylor, S.; Cherry, M.; Fisher, M.; Boxall, K.; Burns, S.; Walton, M. I.; Westwood, I. M.; Hayes, A.; Eve, P.; Valenti, M.; de Haven Brandon, A.; Box, G.; van Montfort, R. L.; Williams, D. H.; Aherne, G. W.; Raynaud, F. I.; Eccles, S. A.; Garrett, M. D.; Collins, I., Structure-guided evolution of potent and selective CHK1 inhibitors through scaffold morphing J. Med. Chem. 2011, 54, 8328-8342). Next, chlorination step was performed according to procedure used previously in our group (Naus, P.; Caletkova, O.; Konecny, P.; Dzubak, P.; Bogdanova, K.; Kolar, M.; Vrbkova, J.; Slavetinska, L.; Tloust'ova, E.; Perlikova, P.;

Hajduch, M.; Hocek, M., Synthesis, cytostatic, antimicrobial, and anti-HCV activity of 6-substituted 7-(het)aryl-7-deazapurine ribonucleosides *J. Med. Chem.* 2014, 57, 1097-110). Modified tricyclic nucleobases were then converted to benzoylated 4-chloropyridopyrrolopyrimidine ribonucleosides 13 or 14 under Vorbrüggen conditions (Scheme 1).

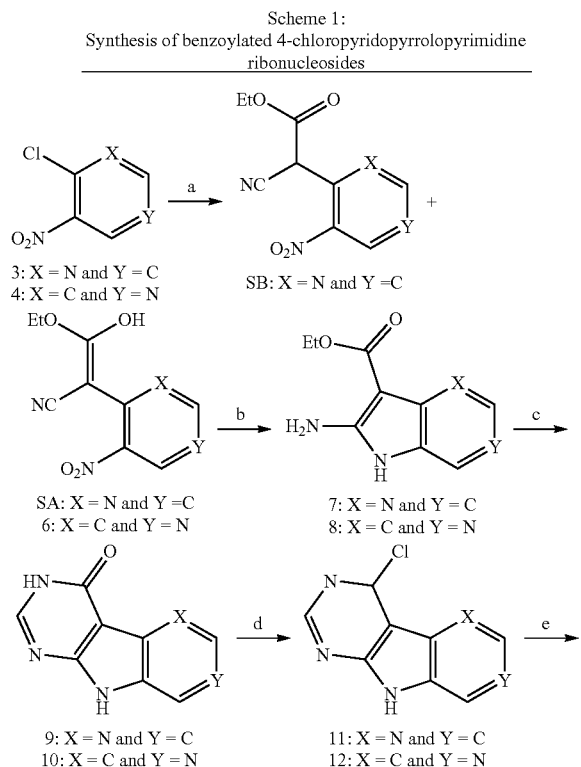

Scheme 1:
Synthesis of benzoylated 4-chloropyridopyrrolopyrimidine ribonucleosides

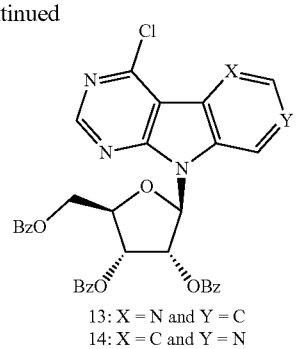

13: X = N and Y = C
14: X = C and Y = N a: *t*BuOK, ethyl cyanoacetate, *t*BuOH, 95° C., 6 h;
b: Zn dust, AcOH, 95° C., 75 min;
c: formamide, HCOONH$_4$, 170° C., 16 h;
d: *N*,*N*-dimethylaniline, benzyltriethylammonium chloride (BTEACl), POCl$_3$, MeCN, 90° C., 1 h;
e: BSA, MeCN, 60° C., 30 min; then 1-*O*-acetyl-2,3,5-tri-*O*-benzoyl-β-D-ribofuranose, TMSOTf, 60° C., 16 h Desired 4-substituted pyridopyrrolopyrimidine ribonucleosides (Scheme 2 and 3) were prepared using Pd-catalyzed cross-coupling reactions or nucleophilic substitutions. Methyl derivatives were synthesized by palladium-catalyzed alkylation of 4-halogenated nucleosides with trimethylaluminium and dimethylaminoderivative by nucleophilic substitution with dimethylamine 2-Furyl group was introduced into position 4 by Stille coupling with 2-furyltributylstannane, 3-furyl, 3-thiophenyl and 2-benzofuryl groups by Suzuki reaction with corresponding boronic acids. All these reactions led to benzoylated derivatives, which gave target free nucleosides by deprotection under Zemplén conditions using sodium methoxide in methanol. Methoxy, amino and methylsulfanyl groups were introduced by nucleophilic substitution, simultaneous debenzoylation occurred under reaction conditions affording deprotected nucleosides.

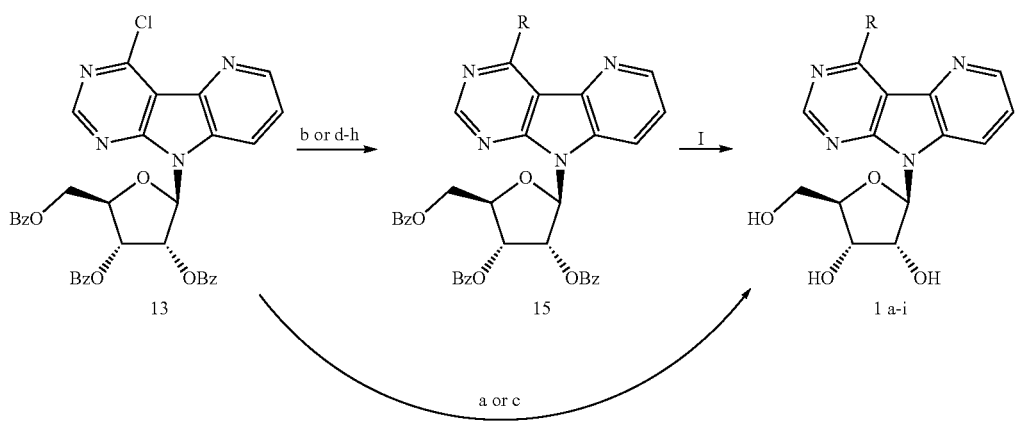

Scheme 2: Synthesis of 4-substituted pyridopyrrolopyrimidine nucleosides 15, 1 a: MeONa, MeOH:DMF, 90° C., 16 h;
b: NaSMe, DMF, rt, 16 h;
c: NH$_3$(aq.), 1,4-dioxane, 120° C., 24 h;
d: Me$_2$NH in THF, *i*PrOH:DCM 1:1, rt, 16 h;
e: Me$_3$Al, Pd(PPh$_3$)$_4$, THF, 70° C., 16 h;
f: 2-tributylstannylfuran, PdCl$_2$(PPh$_3$)$_2$, DMF, 100° C., 4 h;
g: R-boronic acid, Pd(PPh$_3$)$_4$, K$_2$CO$_3$, toluene, 100° C., 4-24 h;
h: R-boronic acid, Pd(PPh$_3$)$_2$Cl$_2$, K$_2$CO$_3$, Et$_3$N, toluene, 100° C., 24 h;
I: MeONa, MeOH:DMF, rt - 90° C., 16 h

TABLE 1

Synthesis of 4-substituted pyridopyrrolopyrimidine nucleosides 15, 1

| Entry | Conditions | R | Protected nucleoside | Yield [%] | Deprotected nucleoside | Yield [%] |
|---|---|---|---|---|---|---|
| 1 | a | OMe | — | — | 1a | 62 |
| 2 | b | SMe | 15b | 52 | 1b | 50 |
| 3 | c | $NH_2$ | — | — | 1c | 52 |
| 4 | e | Me | 15d | 69 | 1d | 87 |
| 5 | d | $NMe_2$ | 15e | 82 | 1e | 81 |
| 6 | f | furan-2-yl | 15f | 90 | 1f | 75 |
| 7 | g | furan-3-yl | 15g | 73 | 1g | 78 |
| 8 | g | thiophen-3-yl | 15h | 70 | 1h | 70 |
| 9 | h | benzofuran-2-yl | 15i | 56 | 1i | 69 |

Scheme 3: Synthesis of 4-substituted pyridopyrrolopyrimidine nucleosides 16, 2

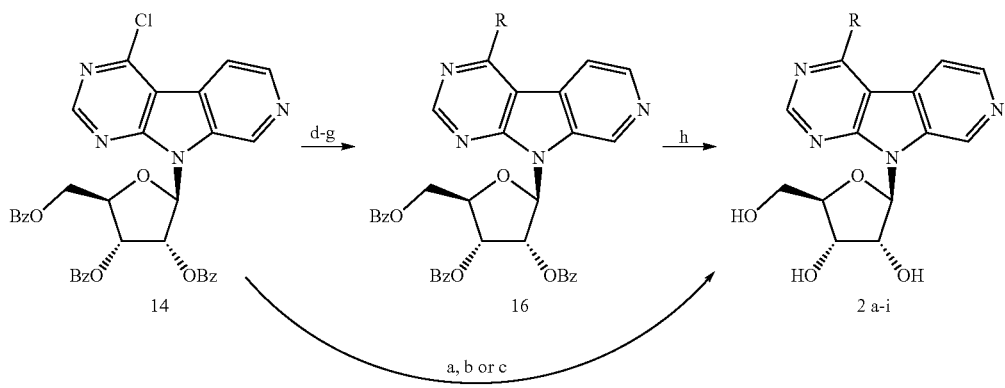

a: MeONa, MeOH, rt, 16 h;
b: NaSMe, MeOH, rt, 16 h;
c: $NH_3$(aq.), 1,4-dioxane, 120° C., 24 h;
d: $Me_2NH$ in THF, iPrOH:DCM 1:1, rt, 16 h;
e: $Me_3Al$, $Pd(PPh_3)_4$, THF, 70° C., 16 h;
f: 2-tributylstannylfuran, $PdCl_2(PPh_3)_2$, DMF, 100° C., 4 h;
g: R-boronic acid, $Pd(PPh_3)_4$, $K_2CO_3$, toluene, 100° C., 3-18 h;
h: MeONa, MeOH:DMF, rt - 60° C., 16 h

TABLE 2

Synthesis of 4-substituted pyridopyrrolopyrimidine nucleosides 16, 2

| Entry | Conditions | R | Protected nucleoside | Yield [%] | Deprotected nucleoside | Yield [%] |
|---|---|---|---|---|---|---|
| 1 | a | OMe | — | — | 2a | — |
| 2 | b | SMe | — | — | 2b | — |
| 3 | c | $NH_2$ | — | — | 2c | — |
| 4 | e | Me | 16d | 55 | 2d | 63 |
| 5 | d | $NMe_2$ | 16e | 67 | 2e | 91 |
| 6 | f | furan-2-yl | 16f | 66 | 2f | 71 |
| 7 | g | furan-3-yl | 16g | 84 | 2g | 90 |
| 8 | g | thiophen-3-yl | 16h | 57 | 2h | 72 |
| 9 | g | benzofuran-2-yl | 16i | 64 | 2i | 79 |

If tested compounds showed activity in in vitro cytotoxic test, it was selective against broad spectrum of cancer cell lines of various histogenetic origin (mesenchymal or epitelial tumors) with significantly lower activity against normal human fibroblasts (BJ and MRC-5 cell lines). A better therapeutic index, low toxicity to non-cancer cell lines, compared to furopyrrolopyrimidine, 5-methylpyrrolopyrrolopyrimidine and thienopyrrolopyrimidine ribonucleosides, together with a different mechanism of action, favors the present compounds as novel cytotoxic agents. Active compounds showed significant submicromolar in vitro cytotoxic activities.

EXAMPLES

List of Abbreviations aq. aqueous
bd broad doublet
bq broad quartet
bs broad singlet
bt broad triplet
btd broad triplet of doublets
Bz benzoyl
C-18 C-18 reverse phase as stationary phase
calcd calculated
d doublet
dd doublet of doublets
ddd doublet of doublet of doublets
DMF N,N-dimethylformamide
DMSO dimethylsulfoxide
dt doublet of triplets
eq. equivalent ESI electrospray ionization
Et ethyl
EtOH ethanol
FT Fourier transform
HPFC high performance flash chromatography
HPLC high-performance liquid chromatography
HR high resolution
iPr isopropyl
IR infrared spectroscopy
m multiplet
Me methyl
MeCN acetonitrile
MeOH methanol
MeONa sodium methoxide
MeSNa sodium thiomethoxide
m.p. melting point
MS mass spectrometry
MTT 3-(4,5-dimethylthiazol-2-yl)-2,5-diphenyltetrazolium bromide
ν wave number
NMR nuclear magnetic resonance
Ph phenyl
q quartet
r.t room temperature
s singlet
$SiO_2$ silicagel as stationary phase
t triplet
td triplet of doublets
TMSOTf trimethylsilyl trifluoromethansulfonate
TFA trifluoroacetic acid
THF tetrahydrofuran General Experimental Part NMR spectra were recorded on a 400 MHz ($^1$H at 400 MHz, $^{13}$C at 100.6 MHz), a 500 MHz ($^1$H at 500 MHz, $^{13}$C at 125.7 MHz), or a 600 MHz ($^1$H at 600 MHz, $^{13}$C at 150.9 MHz) spectrometer. Melting points were determined on a Stuart SMP40 and are uncorrected. Optical rotations were measured at 25° C., and $[\alpha]_D^{20}$ values are given in $10^{-1}$ deg $cm^2$ $g^{-1}$. High resolution mass spectra were measured using ESI, EI or APCI techniques. Reverse-phase high performance flash chromatography (HPFC) was performed on Reverse Phase (C18) RediSep Rf columns on ISCO CombiFlash Rf. FT IR spectra were measured on Bruker Alpha spectrometer using ATR technique. The purity of all tested compounds was confirmed by HPLC analysis and was >95%.

TABLE 3

List of Compounds in Examples

| Example | Compound | Structure | Systematic name |
|---|---|---|---|
| 1 | 1a | OMe-substituted structure | 4-methoxy-9-(β-D-ribofuranosyl)-9H-pyrido[2',3':4,5]pyrrolo[2,3-d]pyrimidine |
| 2 | 1b | SMe-substituted structure | 4-(methylsulfanyl)-9-(β-D-ribofuranosyl)-9H-pyrido[2',3':4,5]pyrrolo[2,3-d]pyrimidine |
| 3 | 1c | $NH_2$-substituted structure | 4-amino-9-(β-D-ribofuranosyl)-9H-pyrido[2',3':4,5]pyrrolo[2,3-d]pyrimidine |

TABLE 3-continued

List of Compounds in Examples

| Example | Compound | Structure | Systematic name |
|---------|----------|-----------|-----------------|
| 4 | 1d | 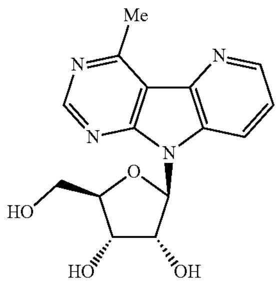 [SMILES: Cc1ncnc2c1c1ncccc1n2[C@@H]1O[C@H](CO)[C@@H](O)[C@H]1O] | 4-methyl-9-(β-D-ribofuranosyl)-9H-pyrido[2',3':4,5]pyrrolo[2,3-d]pyrimidine |
| 5 | 1e | 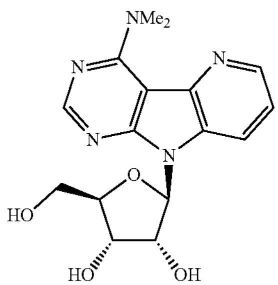 [SMILES: CN(C)c1ncnc2c1c1ncccc1n2[C@@H]1O[C@H](CO)[C@@H](O)[C@H]1O] | 4-(dimethylamino)-9-(β-D-ribofuranosyl)-9H-pyrido[2',3':4,5]pyrrolo[2,3-d]pyrimidine |
| 6 | 1f | 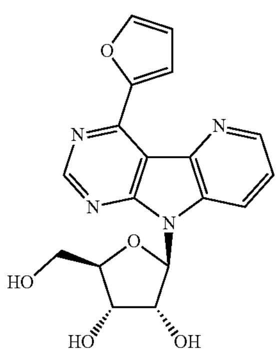 [SMILES: OC[C@H]1O[C@@H](n2c3cccnc3c3c(-c4ccco4)ncnc32)[C@H](O)[C@@H]1O] | 4-(furan-2-yl)-9-(β-D-ribofuranosyl)-9H-pyrido[2',3':4,5]pyrrolo[2,3-d]pyrimidine |
| 7 | 1g | 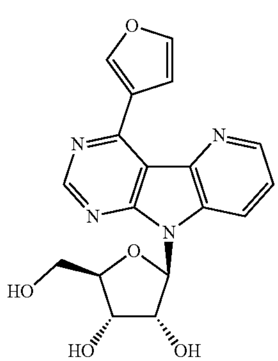 [SMILES: OC[C@H]1O[C@@H](n2c3cccnc3c3c(-c4ccoc4)ncnc32)[C@H](O)[C@@H]1O] | 4-(furan-3-yl)-9-(β-D-ribofuranosyl)-9H-pyrido[2',3':4,5]pyrrolo[2,3-d]pyrimidine |

TABLE 3-continued
List of Compounds in Examples
| Example | Compound | Structure | Systematic name |
|---|---|---|---|
| 8 | 1h | 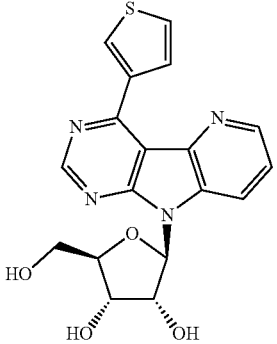 | 4-(thiophen-3-yl)-9-(β-D-ribofuranosyl)-9H-pyrido[2',3':4,5]pyrrolo[2,3-d]pyrimidine |
| 9 | 1i | 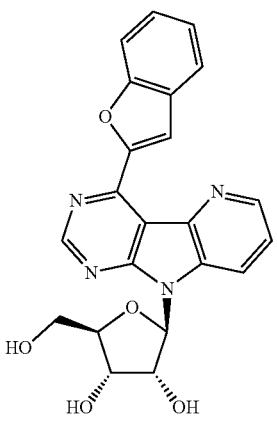 [SMILES: OC[C@H]1O[C@@H](n2c3cccnc3c3c(-c4cc5ccccc5o4)ncnc32)[C@H](O)[C@@H]1O] | 4-(benzofuran-2-yl)-9-(β-D-ribofuranosyl)-9H-pyrido[2',3':4,5]pyrrolo[2,3-d]pyrimidine |
| 10 | 2a | 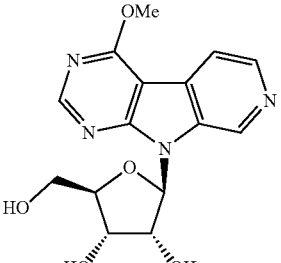 | 4-methoxy-9-(β-D-ribofuranosyl)-9H-pyrido[4',3':4,5]pyrrolo[2,3-d]pyrimidine |
| 11 | 2b | 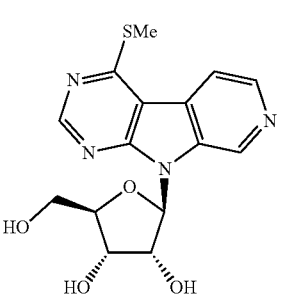 [SMILES: CSc1ncnc2c1c1ccncc1n2[C@@H]1O[C@H](CO)[C@@H](O)[C@H]1O] | 4-(methylsulfanyl)-9-(β-D-ribofuranosyl)-9H-pyrido[4',3':4,5]pyrrolo[2,3-d]pyrimidine |

TABLE 3-continued

List of Compounds in Examples

| Example | Compound | Structure | Systematic name |
|---|---|---|---|
| 12 | 2c | 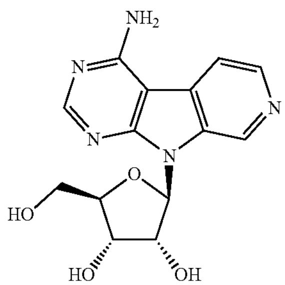 [SMILES: Nc1ncnc2c1c1ccncc1n2[C@@H]1O[C@H](CO)[C@@H](O)[C@H]1O] | 4-amino-9-(β-D-ribofuranosyl)-9H-pyrido[4',3':4,5]pyrrolo[2,3-d]pyrimidine |
| 13 | 2d | 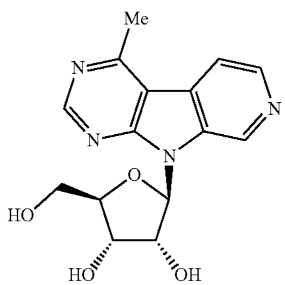 [SMILES: Cc1ncnc2c1c1ccncc1n2[C@@H]1O[C@H](CO)[C@@H](O)[C@H]1O] | 4-methyl-9-(β-D-ribofuranosyl)-9H-pyrido[4',3':4,5]pyrrolo[2,3-d]pyrimidine |
| 14 | 2e | 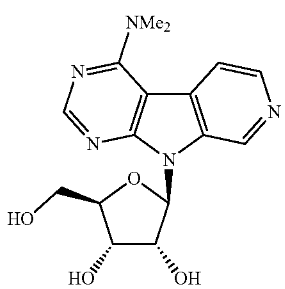 | 4-(dimethylamino)-9-(β-D-ribofuranosyl)-9H-pyrido[4',3':4,5]pyrrolo[2,3-d]pyrimidine |
| 15 | 2f | 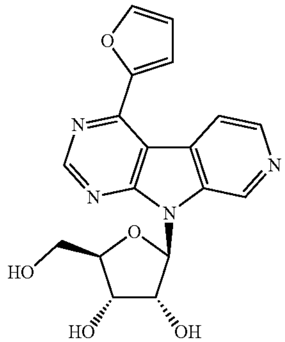 [SMILES: OC[C@H]1O[C@@H](n2c3cnccc3c3c(-c4ccco4)ncnc32)[C@H](O)[C@@H]1O] | 4-(furan-2-yl)-9-(β-D-ribofuranosyl)-9H-pyrido[4',3':4,5]pyrrolo[2,3-d]pyrimidine |
| 16 | 2g | 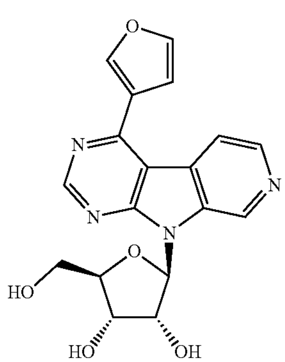 [SMILES: OC[C@H]1O[C@@H](n2c3cnccc3c3c(-c4ccoc4)ncnc32)[C@H](O)[C@@H]1O] | 4-(furan-3-yl)-9-(β-D-ribofuranosyl)-9H-pyrido[4',3':4,5]pyrrolo[2,3-d]pyrimidine |

TABLE 3-continued

List of Compounds in Examples

| Example | Compound | Structure | Systematic name |
|---|---|---|---|
| 17 | 2h | 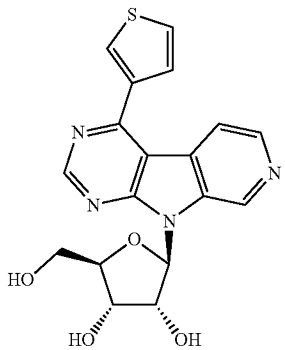 [SMILES: OC[C@H]1O[C@@H](n2c3cnccc3c3c(-c4ccsc4)ncnc32)[C@H](O)[C@@H]1O] | 4-(thiophen-3-yl)-9-(β-D-ribofuranosyl)-9H-pyrido[4',3':4,5]pyrrolo[2,3-d]pyrimidine |
| 18 | 2i | 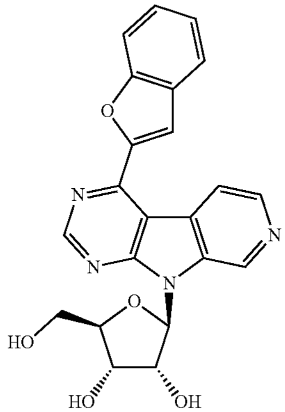 [SMILES: OC[C@H]1O[C@@H](n2c3cnccc3c3c(-c4cc5ccccc5o4)ncnc32)[C@H](O)[C@@H]1O] | 4-(benzofuran-2-yl)-9-(β-D-ribofuranosyl)-9H-pyrido[4',3':4,5]pyrrolo[2,3-d]pyrimidine |

General Procedure A (Stille Coupling)

Protected nucleoside 13 or 14, tributylstannane (1.5 eq.) and $PdCl_2(PPh_3)_2$ (0.1 eq.) were dissolved in anhydrous DMF and heated to 100° C. for 4 to 24 hours. The volatiles were removed in vacuo and the reaction mixture was purified by HPFC ($SiO_2$, ethyl acetate in petroleum ether 0-60%).

Example 1

(Z)-3-Ethoxy-3-hydroxy-2-(3-nitropyridin-2-yl)acrylonitril (5A) and ethyl 2-cyano-2-(3-nitropyridin-2-yl)acetate (5B)

Mixture of tautomers 5A and 5B was prepared by modified known conditions (Finch, N.; Robinson, M. M.; Valerio, M. P. A Synthesis of 4-Azaoxindole *J. Org. Chem.* 1972, 37, 51-53). To a stirred solution of potassium tert-butoxide (4.4 g, 38.0 mmol) in tert-butyl alcohol (40 mL) was added ethyl cyanoacetate (4 mL, 37.8 mmol). To the resultant suspension was added a hot solution of 2-chloro-3-nitropyridine (3 g, 18.9 mmol) in tert-butyl alcohol (40 mL) and the mixture was stirred at 100° C. for 6 h. pH was adjusted to 1 by HCl (1 M) and mixture was extracted with ethyl acetate. Organic layers were evaporated and the crude material was purified by column chromatography on silica (petroleum ether/EtOAc 0→60%) to obtain products 5A and 5B (3.8 g, 87%) as red crystals after recrystallization from ethyl acetate.

$R_f$=0.52 ($SiO_2$; petroleum ether/EtOAc 3:1), Major 5A: $^1$H NMR (500.0 MHz, DMSO-$d_6$): 1.25 (t, 3H, $J_{vic}$=7.1, $CH_3CH_2O$); 4.20 (q, 2H, $J_{vic}$=7.1, $CH_3CH_2O$); 7.02 (dd, 1H, $J_{5,4}$=7.8, $J_{5,6}$=6.1, H-5); 8.37 (dd, 1H, $J_{6,5}$=6.1, $J_{6,4}$=1.6, H-6); 8.45 (dd, 1H, $J_{4,5}$=7.8, $J_{4,6}$=1.6, H-4); 14.47 (bs, 1H, OH); $^{13}$C NMR (125.7 MHz, DMSO-$d_6$): 14.56 ($CH_3CH_2O$); 60.34 ($CH_3CH_2O$); 61.20 (C—CN); 112.43 (CH-5); 116.48 (CN); 138.97 (CH-4); 140.19 (C-3); 142.24 (CH-6); 146.40 (C-2); 168.40 (OCOEt).

Minor 5B: $^1$H NMR (500.0 MHz, DMSO-$d_6$): 1.19 (t, 3H, $J_{vic}$=7.1, $CH_3CH_2O$); 4.23 (q, 2H, $J_{vic}$=7.1, $CH_3CH_2O$); 6.39 (bs, 1H, CHCN); 7.86 (bdd, 1H, $J_{5,4}$=7.9, $J_{5,6}$=4.2, H-5); 8.68 (bd, 1H, $J_{4,5}$=7.9, H-4); 8.98 (dd, 1H, $J_{6,5}$=4,2, H-6); 14.47 (bs, 1H, OH); $^{13}$C NMR (125.7 MHz, DMSO-$d_6$): 13.92 ($CH_3CH_2O$); 45.15 (CHCN); 66.34 ($CH_3CH_2O$); 114.79 (CN); 126.10 (CH-5); 134.70 (CH-4); 144.79 (C-2); 154.00 (CH-6); 163.78 (OCOEt); signal of C-3 hidden by the noise. HR-ESI-MS: m/z (%): 236.0672 (100, [M+H]$^+$, calcd for $C_{10}H_{10}O_4N_3^+$: 236.0671).

Example 2

(Z)-3-Ethoxy-3-hydroxy-2-(3-nitropyridin-4-yl)acrylonitrile (6)

The compound 6 was prepared as described above for derivative 5A and 5B in example 1. Crude material was purified by column chromatography on silica (petroleum ether/EtOAc 0→90%) to obtain product 6 (705 mg, 95%) as an orange foam.

$R_f$=0.21 (SiO$_2$; EtOAc); $^1$H NMR (500.0 MHz, DMSO-d$_6$): 1.18 (t, 3H, J$_{vic}$=7.1, CH$_3$CH$_2$O); 4.05 (q, 2H, J$_{vic}$=7.1, CH$_3$CH$_2$O); 7.60 (bm, 1H, H-5); 7.89 (dd, 1H, J$_{6,5}$=7.1, J$_{6,2}$=1.1, H-6); 8.69 (d, 1H, J$_{2,6}$=1.1, H-2); 13.31 (bs, 1H, OH); $^{13}$C NMR (125.7 MHz, DMSO-d$_6$): 14.65 (CH$_3$CH$_2$O); 59.60 (CH$_3$CH$_2$O); 70.30 (C—CN); 117.89 (CH-5); 119.41 (CN); 136.57 (CH-6); 137.03 (C-3); 138.61 (CH-2); 145.58 (C-4); 165.14 (OCOEt); HR-ESI-MS: m/z (%): 236.0664 (100, [M+H]$^+$, calcd for C$_{10}$H$_{10}$O$_4$N$_3$$^+$: 236.0665); HR-ESI-MS: m/z (%): 258.0484 (100, [M+Na]$^+$, calcd for C$_{10}$H$_9$O$_4$N$_3$Na$^+$: 258.0485).

Example 3

Ethyl 2-amino-1H-pyrrolo[3,2-b]pyridine-3-carboxylate (7)

The compound 7 was prepared according to modified literature procedure (Reader, J. C.; Matthews, T. P.; Klair, S.; Cheung, K. M.; Scanlon, J.; Proisy, N.; Addison, G.; Ellard, J.; Piton, N.; Taylor, S.; Cherry, M.; Fisher, M.; Boxall, K.; Burns, S.; Walton, M. I.; Westwood, I. M.; Hayes, A.; Eve, P.; Valenti, M.; de Haven Brandon, A.; Box, G.; van Montfort, R. L.; Williams, D. H.; Aherne, G. W.; Raynaud, F. I.; Eccles, S. A.; Garrett, M. D.; Collins, I., Structure-guided evolution of potent and selective CHK1 inhibitors through scaffold morphing *J. Med. Chem.* 2011, 54, 8328-8342). A mixture of tautomers 5A and 5B (4.3 g, 18.3 mmol) in AcOH (50 mL) was heated to 95° C. under argon. Zinc dust (5.9 g, 91.5 mmol) was added, and then the reaction mixture was heated at 95° C. for 75 min. Upon cooling, the insoluble material was filtered off through a pad of Celite and washed with fresh AcOH. The filtrate was concentrated, and the residue was treated with saturated solution of NaHCO$_3$ to give a light brown solid. This was filtered, washed with water, and dried to give 7 as a light brown solid (3.5 g, 94%). $R_f$=0.32 (SiO$_2$; EtOAc/MeOH 1:1); $^1$H NMR (500.0 MHz, DMSO-d$_6$): 1.27 (t, 3H, J$_{vic}$=7.1, CH$_3$CH$_2$O); 4.23 (q, 2H, J$_{vic}$=7.1, CH$_3$CH$_2$O); 6.83 (dd, 1H, J$_{6,7}$=7.8, J$_{6,5}$=4.9, H-6); 7.06 (bs, 2H, NH$_2$); 7.35 (dd, 1H, J$_{7,6}$=7.8, J$_{7,5}$=1.5, H-7); 8.07 (dd, 1H, J$_{5,6}$=4.9, J$_{5,7}$=1.5, H-5); 10.80 (bs, 1H, NH); $^{13}$C NMR (125.7 MHz, DMSO-d$_6$): 15.13 (CH$_3$CH$_2$O); 58.27 (CH$_3$CH$_2$O); 84.32 (C-3); 114.54 (CH-6); 115.43 (CH-7); 126.57 (C-7a); 141.62 (CH-5); 145.49 (C-3a); 155.79 (C-2); 165.62 (COOEt); HR-ESI-MS: m/z (%): 206.0924 (100, [M+H]$^+$, calcd for C$_{10}$H$_{12}$O$_2$N$_3$$^+$: 206.0924).

Example 4

Ethyl 2-amino-1H-pyrrolo[2,3-c]pyridine-3-carboxylate (8)

The compound 8 was prepared as described above for derivative 7 in example 3, from compound 6 (2.9 g, 12.3 mmol). After filtration, compound 8 (1.8 g, 73%) was obtained as a brown solid. $R_f$=0.26 (SiO$_2$; EtOAc/MeOH 1:1); $^1$H NMR (500.0 MHz, DMSO-d$_6$): 1.32 (t, 3H, J$_{vic}$=7.1, CH$_3$CH$_2$O); 4.23 (q, 2H, J$_{vic}$=7.1, CH$_3$CH$_2$O); 7.04 (s, 2H, NH$_2$); 7.42 (dd, 1H, J$_{4,5}$=5.2, J$_{4,7}$=1.0, H-4); 8.03 (d, 1H, J$_{5,4}$=5.2, H-5); 8.30 (t, 1H, J$_{4,7}$=J$_{4,NH}$=1.0, H-7); 10.92 (bs, 1H, NH); $^{13}$C NMR (125.7 MHz, DMSO-d$_6$): 14.88 (CH$_3$CH$_2$O); 58.65 (CH$_3$CH$_2$O); 83.91 (C-3); 112.71 (CH-4); 130.44 (C-7a); 130.90 (CH-7); 132.78 (C-3a); 140.65 (CH-5); 155.01 (C-2); 165.67 (COOEt); HR-ESI-MS: m/z (%): 206.0922 (100, [M+H]$^+$, calcd for C$_{10}$H$_{12}$O$_2$N$_3$$^+$: 206.0924).

Example 5

3,9-Dihydro-4H-pyrido[2',3':4,5]pyrrolo[2,3-d]pyrimidin-4-one (9)

A mixture of 7 (3.2 g, 15.6 mmol) and ammonium formate (1.1 g, 17.5 mmol) in formamide (25 mL, 624 mmol) was heated at 170° C. for 16 h. 1 M HCl was added to the cooled reaction mixture, and the resulting suspension was filtered to remove insolubles. The filtrate was then adjusted to pH 7 with saturated solution of NaHCO$_3$. The resulting precipitate was collected by filtration, washed with water and dried to give 9 (2.5 g, 86%) as a brown solid.

$R_f$=0.67 (SiO$_2$; EtOAc/MeOH 1:1); $^1$H NMR (500.0 MHz, DMSO-d$_6$): 7.31 (dd, 1H, J$_{7,8}$=8.2, J$_{7,6}$=4.7, H-7); 7.83 (dd, 1H, J$_{8,7}$=8.2, J$_{8,6}$=1.5, H-8); 8.18 (s, 1H, H-2); 8.47 (dd, 1H, J$_{6,7}$=4.7, J$_{6,8}$=1.5, H-6); 12.27, 12.39 (2×bs, 2×1H, NH-3,9); $^{13}$C NMR (125.7 MHz, DMSO-d$_6$): 99.94 (C-4a); 119.07 (CH-8); 119.31 (CH-7); 129.26 (C-8a); 141.10 (C-4b); 144.11 (CH-6); 149.37 (CH-2); 155.30 (C-9a); 157.58 (C-4); HR-ESI-MS: m/z (%): 187.0612 (100, [M+H]$^+$, calcd for C$_9$H$_7$ON$_4$$^+$: 187.0614).

Example 6

3,9-Dihydro-4H-pyrido[4',3':4,5]pyrrolo[2,3-d]pyrimidin-4-one (10)

The compound 10 was prepared as described above for derivative 9 in example 5, from compound 8 (2.1 g, 10.2 mmol). After filtration, compound 10 was obtained as a brown solid (1.5 g, 79%).

$R_f$=0.69 (SiO$_2$; EtOAc/MeOH 1:1); $^1$H NMR (400.0 MHz, DMSO-d$_6$): 7.89 (d, 1H, J$_{5,6}$=5.2, H-5); 8.26 (s, 1H, H-2); 8.38 (d, 1H, J$_{6,5}$=5.2, H-6); 8.83 (s, 1H, H-8); 12.44, 12.58 (2×s, 2×1H, NH-3,9); $^{13}$C NMR (125.7 MHz, DMSO-d$_6$): 99.62 (C-4a); 115.08 (CH-5); 127.64 (C-4b); 132.35 (C-8a); 134.39 (CH-8); 140.66 (CH-6); 150.19 (CH-2); 155.41 (C-9a); 158.54 (C-4); HR-ESI-MS: m/z (%): 187.0613 (100, [M+H]$^+$, calcd for C$_9$H$_7$ON$_4$$^+$: 187.0614).

Example 7

4-Chloro-9H-pyrido[2',3':4,5]pyrrolo[2,3-d]pyrimidine (11)

Tricyclic modified nucleobase 11 was prepared according to modified literature procedure (Liu, J.; Janeba, Z.; Robins, M. J. SNAr Iodination of 6-Chloropurine Nucleosides: Aromatic Finkelstein Reactions at Temperatures Below −40° C. *Org. Lett.* 2004, 6, 2917-2919.) POCl$_3$ (0.2 mL, 2.4 mmol) was added to a stirred solution of 9 (80 mg, 0.4 mmol), benzyltriethylammonium chloride (196 mg, 0.8 mmol) and N,N-dimethylaniline (62 µL, 0.5 mmol) in MeCN (1 mL), and stirring continued for 1 h at 90° C. Volatiles were evaporated, cold water was added and pH was adjusted to 4-5 by 35% aq. NH$_3$. Mixture was extracted with ethyl acetate and organic phase was dried (Na$_2$SO$_4$). Solvent was evaporated and the residue was stirred for 16 h with petroleum ether (to remove the rest of N,N-dimethylaniline) The resulting solid was collected by filtration, washed with petroleum ether and dried to give 11 (57 mg, 65%) as a yellowish solid.

$R_f$=0.42 (SiO$_2$; EtOAc); $^1$H NMR (500.0 MHz, DMSO-d$_6$): 7.61 (dd, 1H, J$_{7,8}$=8.3, J$_{7,6}$=4.7, H-7); 8.04 (dd, 1H, J$_{8,7}$=8.3, J$_{8,6}$=1.4, H-8); 8.69 (dd, 1H, J$_{6,7}$=4.7, J$_{6,8}$=1.4, H-6); 8.87 (s, 1H, H-2); 12.97 (s, 1H, NH); $^{13}$C NMR (125.7

MHz, DMSO-$d_6$): 110.29 (C-4a); 120.08 (CH-8); 122.97 (CH-7); 132.81 (C-8a); 136.88 (C-4b); 144.66 (CH-6); 152.13 (C-4); 155.49 (CH-2); 156.30 (C-9a); HR-ESI-MS: m/z (%): 205.0275 (100, [M+H]$^+$, calcd for $C_9H_6N_4Cl^+$: 205.0275).

Example 8

4-Chloro-9H-pyrido[4',3':4,5]pyrrolo[2,3-d]pyrimidine (12)

The compound 12 was prepared as described above for derivative 11 in example 7, from compound 10 (572 mg, 3.1 mmol). After adjusting pH to 4-5 by NH$_3$ (35%), solvent was evaporated and the crude material was purified by column chromatography on silica (CHCl$_3$/MeOH 0→10%) to obtain product 12 (330 mg, 52%) as a yellow solid.

$R_f$=0.17 (SiO$_2$; EtOAc); $^1$H NMR (500.0 MHz, DMSO-$d_6$): 8.18 (dd, 1H, $J_{5,6}$=5.3, $J_{5,8}$=1.2, H-5); 8.60 (d, 1H, $J_{6,5}$=5.3, H-6); 8.92 (s, 1H, H-2); 9.03 (d, 1H, $J_{8,5}$=1.2, H-8); 13.15 (s, 1H, NH); $^{13}$C NMR (125.7 MHz, DMSO-$d_6$): 110.17 (C-4a); 116.35 (CH-5); 123.62 (C-4b); 134.60 (CH-8); 135.44 (C-8a); 141.49 (CH-6); 153.93 (C-4); 156.44 (CH-2); 156.54 (C-9a); HR-ESI-MS: m/z (%): 205.0274 (100, [M+H]$^+$, calcd for $C_9H_6N_4Cl^+$: 205.0275).

Example 9

4-Chloro-9-(2,3,5-tri-O-benzoyl-β-D-ribofuranosyl)-9H-pyrido[2',3:4,5]pyrrolo[2,3-d]pyrimidine (13)

To a solution of a tricyclic base 11 (234 mg; 1.1 mmol) in MeCN (20 mL), BSA (281 μL, 1.1 mmol) was added. The reaction mixture was heated at 60° C. for 30 min, then, TMSOTf (397 μL, 2.2 mmol) and 1-O-acetyl-2,3,5-tri-O-benzoyl-β-D-ribofuranose (1.1 g, 2.2 mmol) were added. The reaction mixture was heated to 60° C. for 16 h. After that, the mixture was cooled and then extracted with DCM. The organic fraction was washed with saturated solution of NaHCO$_3$, water, dried over Na$_2$SO$_4$ and evaporated under reduced pressure. The crude material was purified using column chromatography (petroleum ether/EtOAc 0→45%). Desired nucleoside 13 (535 mg, 75%) was obtained as a straw foam. $R_f$=0.37 (SiO$_2$; petroleum ether/EtOAc 3:2); $^1$H NMR (400.0 MHz, DMSO-$d_6$): 4.73 (dd, 1H, $J_{gem}$=12.3, $J_{5'b,4'}$=4.4, 4.4, H-5'b); 4.87 (dd, 1H, $J_{gem}$=12.3, $J_{5'a,4'}$=3.2, H-5'a); 4.93 (ddd, 1H, $J_{4',3'}$=6.6, $J_{4',5'}$=4.4, 3.2, H-4'); 6.37 (t, 1H, $J_{3',2'}$=$J_{3',4'}$=6.5, H-3'); 6.55 (dd, 1H, $J_{2',3'}$=6.5, $J_{2',1'}$=4.6, H-2'); 7.06 (d, 1H, $J_{1',2'}$=4.6, H-1'); 7.43, 7.51 (2×m, 6H, H-m-Bz); 7.58 (dd, 1H, $J_{7,8}$=8.5, $J_{7,6}$=4.7, H-7); 7.62, 7.67, 7.68 (3×m, 3×1H, H-p-Bz); 7.83, 7.92, 7.99 (3×m, 3×2H, H-o-Bz); 8.54 (dd, 1H, $J_{8,7}$=8.5, $J_{8,6}$=1.3, H-8); 8.78 (dd, 1H, $J_{6,7}$=4.7, $J_{6,8}$=1.3, H-6); 8.87 (s, 1H, H-2); $^{13}$C NMR (125.7 MHz, DMSO-$d_6$): 63.22 (CH$_2$-5'); 70.29 (CH-3'); 72.63 (CH-2'); 79.03 (CH-4'); 86.26 (CH-1'); 111.45 (C-4a); 119.92 (CH-8); 123.08 (CH-7); 128.64, 128.81 (C-i-Bz); 128.94, 128.98, 129.01 (CH-m-Bz); 129.36 (C-i-Bz); 129.37, 129.54, 129.66 (CH-o-Bz); 132.85 (C-8a); 133.83, 134.15 (CH-p-Bz); 136.92 (C-4b); 145.75 (CH-6); 152.71 (C-4); 155.31 (CH-2); 155.50 (C-9a); 164.81, 165.00, 165.57 (CO-Bz); HR-ESI-MS: m/z (%): 649.1486 (100, [M+H]$^+$, calcd for $C_{35}H_{26}O_7N_4Cl^+$: 649.1484); HR-ESI-MS: m/z (%): 671.1306 (100, [M+Na]$^+$, calcd for $C_{35}H_{25}O_7N_4ClNa^+$: 671.1304).

Example 10

4-Chloro-9-(2,3,5-tri-O-benzoyl-β-D-ribofuranosyl)-9H-pyrido[4',3':4,5]pyrrolo[2,3-d]pyrimidine (14)

The protected nucleoside 14 was prepared as described above for derivative 13 in example 9, from tricyclic base 12 (100 mg; 0.5 mmol). The crude material was purified using column chromatography (cyclohexane/EtOAc 0→50%). Desired protected nucleoside 14 (185 mg, 57%) was obtained as a straw foam.

$R_f$=0.63 (SiO$_2$; petroleum ether/EtOAc 1:2); $^1$H NMR (500.0 MHz, DMSO-$d_6$): 4.74 (dd, 1H, $J_{gem}$=12.3, $J_{5'b,4'}$=4.6, H-5'b); 4.85 (dd, 1H, $J_{gem}$=12.3, $J_{5'a,4'}$=3.2, H-5'a); 4.94 (ddd, 1H, $J_{4',3'}$=6.5, $J_{4',5'}$=4.6, 3.2, H-4'); 6.35 (t, 1H, $J_{3',2'}$=$J_{3',4'}$=6.5, H-3'); 6.58 (dd, 1H, $J_{2',3'}$=6.5, $J_{2',1'}$=4.6, H-2'); 7.13 (d, 1H, $J_{1',2'}$=4.6, H-1'); 7.40-7.44, 7.46-7.52 (2×m, 6H, H-m-Bz); 7.62, 7.66, 7.68 (3×m, 3×1H, H-p-Bz); 7.83-7.86, 7.89-7.92, 7.99-8.02 (3×m, 3×2H, H-o-Bz); 8.27 (dd, 1H, $J_{5,6}$=5.2, $J_{5,8}$=0.9, H-5); 8.71 (d, 1H, $J_{6,5}$=5.2, H-6); 8.92 (s, 1H, H-2); 9.53 (d, 1H, $J_{8,5}$=0.9, H-8); $^{13}$C NMR (125.7 MHz, DMSO-$d_6$): 63.25 (CH$_2$-5'); 70.33 (CH-3'); 72.61 (CH-2'); 79.17 (CH-4'); 86.41 (CH-1'); 111.36 (C-4a); 116.34 (CH-5); 124.05 (C-4b); 128.62, 128.79 (C-i-Bz); 128.90, 128.97 (CH-m-Bz); 129.28 (C-i-Bz); 129.30, 129.51, 129.62 (CH-o-Bz); 133.75, 134.10 (CH-p-Bz); 134.25 (C-8a); 135.16 (CH-8); 142.91 (CH-6); 154.43 (C-4); 155.52 (C-9a); 156.24 (CH-2); 164.79, 165.96, 165.52 (CO-Bz); HR-ESI-MS: m/z (%): 649.1486 (100, [M+H]$^+$, calcd for $C_{35}H_{26}O_7N_4Cl^+$: 649.1484).

Example 11

4-Methoxy-9-(β-D-ribofuranosyl)-9H-pyrido[2',3':4,5]pyrrolo[2,3-d]pyrimidine (1a)

To a suspension of nucleoside 13 (135 mg, 0.2 mmol) in a mixture of MeOH (14 mL) and DMF (14 mL), sodium methoxide (190 μL, 25 wt. % in MeOH, 0.84 mmol) was added. The reaction mixture was stirred for 16 h at 90° C., then MeOH was evaporated and the crude material crystallized from mixture DMF/acetone. Nucleoside 1a (41 mg, 62%) was obtained as a white powder.

$R_f$=0.62 (SiO$_2$; CHCl$_3$/MeOH 5:1); $[\alpha]_D^{20}$=−27.0 (c=0.204 in DMSO); $^1$H NMR (500.0 MHz, DMSO-$d_6$): 3.68 (ddd, 1H, $J_{gem}$=12.0, $J_{5'b,OH}$=5.4, $J_{5'b,4'}$=3.6, H-5'a); 3.71 (ddd, 1H, $J_{gem}$=12.0, $J_{5'a,OH}$=5.1, $J_{5'a,4'}$=3.3, H-5'b); 3.99 (ddd, 1H, $J_{4',5'}$=3.6, 3.3, $J_{4',3'}$=2.5, H-4'); 4.19 (s, 3H, CH$_3$O); 4.20 (ddd, 1H, $J_{3',2'}$=5.4, $J_{3',OH}$=4.7, $J_{3',4'}$=2.5, H-3'); 4.69 (ddd, 1H, $J_{2',1'}$=7.5, $J_{2',OH}$=6.2, $J_{2',3'}$=5.4, H-2'); 5.24 (bd, 1H, $J_{OH,3'}$=4.7, OH-3'); 5.29 (bdd, 1H, $J_{OH,5'}$=5.4, 5.1, OH-5'); 5.31 (bd, 1H, $J_{OH,2'}$=6.2, OH-2'); 6.49 (d, 1H, $J_{1',2'}$=7.5, H-1'); 7.48 (dd, 1H, $J_{7,8}$=8.4, $J_{7,6}$=4.7, H-7); 8.48 (dd, 1H, $J_{8,7}$=8.4, $J_{8,6}$=1.4, H-8); 8.61 (dd, 1H, $J_{6,7}$=4.7, $J_{6,8}$=1.4, H-6); 8.74 (s, 1H, H-2); $^{13}$C NMR (125.7 MHz, DMSO-$d_6$): 54.38 (CH$_3$O); 61.80 (CH$_2$-5'); 70.37 (CH-3'); 71.18 (CH-2'); 85.85 (CH-4'); 86.98 (CH-1'); 98.62 (C-4a); 120.52 (CH-8); 120.84 (CH-7); 130.61 (C-8a); 138.39 (C-4b); 144.55 (CH-6); 155.80 (CH-2); 157.10 (C-9a); 164.01 (C-4); HR-ESI-MS: m/z (%): 333.1194 (100, [M+H]$^+$, calcd for $C_{15}H_{17}O_5N_4^+$: 333.1193); HR-ESI-MS: m/z (%): 355.1013 (100, [M+Na]$^+$, calcd for $C_{15}H_{16}O_5N_4Na^{30}$: 355.1012).

Example 12

4-Methoxy-9-(β-D-ribofuranosyl)-9H-pyrido[4',3':4,5]pyrrolo[2,3-d]pyrimidine (2a)

To a suspension of nucleoside 14 (210 mg, 0.32 mmol) in MeOH (21 mL), sodium methoxide (296 μL, 25 wt. % in MeOH, 1.28 mmol) was added. The reaction mixture was stirred for 16 h at 22° C., then MeOH was evaporated and the crude material was purified using revers phase column chromatography (C-18, water/MeOH 0→100%). Nucleoside 2a (42 mg, 42%) was obtained as a white powder.

$R_f$=0.57 (SiO$_2$; CHCl$_3$/MeOH 5:1); [β]$_D^{20}$=−54.9 (c=0.122 in DMSO); $^1$H NMR (400.0 MHz, DMSO-d$_6$): 3.70 (ddd, 1H, $J_{gem}$=12.0, $J_{5'b,OH}$=5.2, $J_{5'b,4'}$=3.4, H-5'b); 3.74 (ddd, 1H, $J_{gem}$=12.0, $J_{5'a,OH}$=5.0, $J_{5'a,4'}$=3.2, H-5'a); 4.02 (ddd, 1H, $J_{4',5'}$=3.4, 3.2, $J_{4',3'}$=2.6, H-4'); 4.23 (s, 3H, CH$_3$O); 4.23 (ddd, 1H, $J_{3',2'}$=5.7, $J_{3',OH}$=4.6, $J_{3',4'}$=2.6, H-3'); 4.73 (ddd, 1H, $J_{2',1'}$=7.7, $J_{2',OH}$=6.5, $J_{2',3'}$=5.7, H-2'); 5.26 (d, 1H, $J_{OH,3'}$=4.6, OH-3'); 5.29 (dd, 1H, $J_{OH,5'}$=5.2, 5.0, OH-5'); 5.33 (bd, 1H, $J_{OH,2'}$=6.6, OH-2'); 6.51 (d, 1H, $J_{1',2'}$=7.6, H-1'); 7.99 (dd, 1H, $J_{5,6}$=5.2, $J_{5,8}$=1.1, H-5); 8.56 (d, 1H, $J_{6,5}$=5.2, H-6); 8.80 (s, 1H, H-2); 9.43 (d, 1H, $J_{8,5}$=1.1, H-8); $^{13}$C NMR (125.7 MHz, DMSO-d$_6$): 54.73 (CH$_3$O); 61.73 (CH$_2$-5'); 70.29 (CH-3'); 71.49 (CH-2'); 85.96 (CH-4'); 86.99 (CH-1'); 98.06 (C-4a); 116.26 (CH-5); 124.91 (C-4b); 132.87 (C-8a); 135.95 (CH-8); 141.71 (CH-6); 156.88 (CH-2); 157.07 (C-9a); 165.02 (C-4); HR-ESI-MS: m/z (%): 333.1194 (100, [M+H]$^+$, calcd for C$_{15}$H$_{17}$)$_5$N$_4^+$: 333.1193).

Example 13

4-(Methylsulfanyl)-9-(2,3,5-tri-O-benzoyl-β-D-ribofuranosyl)-9H-pyrido[2',3':4,5]pyrrolo[2,3-d]pyrimidine (15b)

To a suspension of nucleoside 13 (350 mg, 0.54 mmol) in DMF (80 mL), sodium thiomethoxide (113 mg, 1.62 mmol) was added. The reaction mixture was stirred for 16 h at 22° C., then solvent was evaporated and the crude material was purified using column chromatography (petroleum ether/EtOAc 0→80%). Protected nucleoside 15b (186 mg, 52%) was obtained as a white powder.

$R_f$=0.77 (SiO$_2$, petroleum ether/EtOAc 1:1); $^1$H NMR (500.0 MHz, DMSO-d$_6$): 2.71 (s, 3H, SCH$_3$); 4.71 (dd, 1H, $J_{gem}$=12.3, $J_{5'b,4'}$=4.3, H-5'b); 4.83 (dd, 1H, $J_{gem}$=12.3, $J_{5'a,4'}$=3.2, H-5'a); 4.89 (ddd, 1H, $J_{4',3'}$=6.5, $J_{4',5'}$=4.3, 3.2, H-4'); 6.36 (t, 1H, $J_{3',2'}$=$J_{3',4'}$=6.5, H-3'); 6.58 (dd, 1H, $J_{2',3'}$=6.5, $J_{2',1'}$=4.7, H-2'); 7.00 (d, 1H, $J_{1',2'}$=4.7, H-1'); 7.41 (m, 2H, H-m-Bz); 7.46 (dd, 1H, $J_{7,8}$=8.4, $J_{7,6}$=4.7, H-7); 7.48-7.52 (m, 4H, H-m-Bz); 7.61, 7.67, 7.68 (3×m, 3×1H, H-p-Bz); 7.83, 7.93, 8.00 (3×m, 3×2H, H-o-Bz); 8.43 (dd, 1H, $J_{8,7}$=8.4, $J_{8,6}$=1.4, H-8); 8.70 (dd, 1H, $J_{6,7}$=4.7, $J_{6,8}$=1.4, H-6); 8.83 (s, 1H, H-2); $^{13}$C NMR (125.7 MHz, DMSO-d$_6$): 11.79 (SCH$_3$); 63.27 (CH$_2$-5'); 70.38 (CH-3'); 72.47 (CH-2'); 78.86 (CH-4'); 86.06 (CH-1'); 109.79 (C-4a); 119.12 (CH-8); 121.47 (CH-7); 128.60, 128.82 (C-i-Bz); 128.89, 128.93, 128.96 (CH-m-Bz); 129.35 (CH-o-Bz); 129.38 (C-i-Bz); 129.48, 129.61 (CH-o-Bz); 131.60 (C-8a); 133.76, 134.09 (CH-p-Bz); 138.54 (C-4b); 145.04 (CH-6); 153.18 (C-9a); 154.89 (CH-2); 164.20 (C-4); 164.76, 164.98, 165.56 (CO-Bz); HR-ESI-MS: m/z (%): 661.1753 (100, [M+H]$^+$, calcd for C$_{36}$H$_{29}$O$_7$N$_4$S$^+$: 661.1751); HR-ESI-MS: m/z (%): 683.1571 (100, [M+Na]$^+$, calcd for C$_{36}$H$_{28}$O$_7$N$_4$NaS$^+$: 683.1570).

Example 14

4-(Methylsulfanyl)-9-β-ribofuranosyl)-9H-pyrido[2',3':4,5]pyrrolo[2,3-d]pyrimidine (1b)

Protected nucleoside 15b (180 mg, 0.3 mmol) was dissolved in a mixture of MeOH (6 mL) and DMF (10 mL), and sodium methoxide (14 μL, 25 wt. % in MeOH, 0.06 mmol) was added. The reaction mixture was stirred at 90° C. for 16 h. Solvent was evaporated under reduced pressure and product was crystallized from MeOH. Nucleoside 1b (79 mg, 76%) was obtained as a white powder.

$R_f$=0.62 (SiO$_2$; CHCl$_3$/MeOH 5:1); [α]$_D^{20}$=−26.7 (c=0.135 in DMSO); $^1$H NMR (500.0 MHz, DMSO-d$_6$): 2.72 (s, 3H, SCH$_3$); 3.69 (ddd, 1H, $J_{gem}$=11.9, $J_{5'b,OH}$=5.3, $J_{5'b,4'}$=3.5, H-5'b); 3.73 (ddd, 1H, $J_{gem}$=11.9, $J_{5'a,OH}$=5.1, $J_{5'a,4'}$=3.3, H-5'a); 4.00 (ddd, 1H, $J_{4',5'}$=3.5, 3.3, $J_{4',3'}$=2.7, H-4'); 4.22 (ddd, 1H, $J_{3',2'}$=5.6, $J_{3',OH}$=4.6, $J_{3',4'}$=2.7, H-3'); 4.70 (ddd, 1H, $J_{2',1'}$=7.5, $J_{2',OH}$=6.3, $J_{2',3'}$=5.6, H-2'); 5.21 (d, 1H, $J_{OH,3'}$=4.6, OH-3'); 5.25 (dd, 1H, $J_{OH,5'}$=5.3, 5.1, OH-5'); 5.29 (d, 1H, $J_{OH,2'}$=6.3, OH-2'); 6.49 (d, 1H, $J_{1',2'}$=7.5, H-1'); 7.52 (dd, 1H, $J_{7,8}$=8.4, $J_{7,6}$=4.7, H-7); 8.51 (dd, 1H, $J_{8,7}$=8.4, $J_{8,6}$=1.4, H-8); 8.69 (dd, 1H, $J_{6,7}$=4.7, $J_{6,8}$=1.4, H-6); 8.91 (s, 1H, H-2); $^{13}$C NMR (125.7 MHz, DMSO-d$_6$): 11.75 (SCH$_3$); 61.74 (CH$_2$-5'); 70.31 (CH-3'); 71.18 (CH-2'); 85.85 (CH-4'); 86.87 (CH-1'); 109.29 (C-4a); 120.56 (CH-8); 121.26 (CH-7); 131.12 (C-8a); 138.78 (C-4b); 144.56 (CH-6); 153.75 (C-9a); 154.88 (CH-2); 163.76 (C-4); HR-ESI-MS: m/z (%): 349.0965 (100, [M+H]$^+$, calcd for C$_{15}$H$_{17}$O$_4$N$_4$S$^+$: 349.0965).

Example 15

4-(Methylsulfanyl)-9-(β-D-ribofuranosyl)-9H-pyrido[4',3':4,5]pyrrolo[2,3-d]pyrimidine (2b)

To a suspension of nucleoside 14 (221 mg, 0.34 mmol) in MeOH (55 mL), sodium thiomethoxide (36 mg, 0.51 mmol) was added. The reaction mixture was stirred at 22° C. for 16 h, then the solvent was evaporated and the crude material was purified by a reverse phase column chromatography (C-18, H$_2$O/MeOH 0→100%). Nucleoside 2b (56 mg, 47%) was obtained as a white powder.

$R_f$=0.57 (SiO$_2$; CHCl$_3$/MeOH 5:1); [β]$_D^{20}$=−64.7 (c=0.221 in DMSO); $^1$H NMR (500.0 MHz, DMSO-d$_6$): 2.82 (s, 3H, SCH$_3$); 3.71 (ddd, 1H, $J_{gem}$=11.9, $J_{5'b,OH}$=5.2, $J_{5'b,4'}$=3.5, H-5'b); 3.74 (ddd, 1H, $J_{gem}$=11.9, $J_{5'a,OH}$=5.2, $J_{5'a,4'}$=3.2, H-5'a); 4.03 (ddd, 1H, $J_{4',5'}$=3.5, 3.2, $J_{4',3'}$=2.7, H-4'); 4.24 (ddd, 1H, $J_{3',2'}$=5.7, $J_{3',OH}$=4.6, $J_{3',4'}$=2.7, H-3'); 4.72 (ddd, 1H, $J_{2',1'}$=7.6, $J_{2',OH}$=6.4, $J_{2',3'}$=5.7, H-2'); 5.23 (d, 1H, $J_{OH,3'}$=4.6, OH-3'); 5.26 (t, 1H, $J_{OH,5'}$=5.2, OH-5'); 5.29 (bd, 1H, $J_{OH,2'}$=6.4, OH-2'); 6.53 (d, 1H, $J_{1',2'}$=7.6, H-1'); 8.05 (dd, 1H, $J_{5,6}$=5.2, $J_{5,8}$=1.1, H-5); 8.63 (d, 1H, $J_{6,5}$=5.2, H-6); 8.96 (s, 1H, H-2); 9.49 (d, 1H, $J_{8,5}$=1.1, H-8); $^{13}$C NMR (125 MHz, DMSO-d$_6$): 11.89 (SCH$_3$); 61.65 (CH$_2$-5'); 70.21 (CH-3'); 71.42 (CH-2'); 85.98 (CH-4'); 86.85 (CH-1'); 108.84 (C-4a); 116.31 (CH-5); 124.92 (C-4b); 132.93 (C-8a); 136.08 (CH-8); 141.86 (CH-6); 153.85 (C-9a); 155.72 (CH-2); 164.97 (C-4); HR-ESI-MS: m/z (%): 349.0965 (100, [M+H]$^+$, calcd for C$_{15}$H$_{17}$O$_4$N$_4$S$^+$: 349.0965).

Example 16

4-Amino-9-(β-D-ribofuranosyl)-9H-pyrido[2',3':4,5]pyrrolo[2,3-d]pyrimidine (1c)

To a solution of nucleoside 13 (300 mg, 0.46 mmol) in a dry 1,4-dioxane (2.2 mL), 30% aq ammonia (6.5 mL) was added. The reaction mixture was heated in a pressure tube at 120° C. for 24 h. After that, solvents were evaporated and the crude material was purified by reverse phase column chromatography (C-18, H$_2$O/MeOH 0→100%). Nucleoside 1c (77 mg, 53%) was obtained as a white powder.

$R_f$=0.13 (SiO$_2$; CHCl$_3$/MeOH 10:1); [α]$_D^{20}$=−20.7 (c=0.140 in MeOH); $^1$H NMR (500.0 MHz, DMSO-d$_6$): 3.65 (ddd, 1H, J$_{gem}$=12.0, J$_{5'b,OH}$=6.4, J$_{5'b,4'}$=3.5, H-5'b); 3.70 (ddd, 1H, J$_{gem}$=12.0, J$_{5'a,OH}$=4.8, J$_{5'a,4'}$=3.2, H-5'a); 4.02 (ddd, 1H, J$_{4',5'}$=3.5, 3.2, J$_{4',3'}$=2.9, H-4'); 4.19 (ddd, 1H, J$_{3',2'}$=5.2, J$_{3',OH}$=4.5, J$_{3',4'}$=2.9, H-3'); 4.72 (ddd, 1H, J$_{2',1'}$=7.5, J$_{2',OH}$=6.6, J$_{2',3'}$=5.2, H-2'); 5.20 (d, 1H, J$_{OH,3'}$=4.5, OH-3'); 5.28 (bd, 1H, J$_{OH,2'}$=6.6, OH-2'); 5.44 (dd, 1H, J$_{OH,5'}$=6.4, 4.8, OH-5'); 6.35 (d, 1H, J$_{1',2'}$=7.5, H-1'); 6.84 (bs, 1H, NH$_a$H$_b$); 7.40 (dd, 1H, J$_{7,8}$=8.3, J$_{7,6}$=4.8, H-7); 7.98 (bs, 1H, NH$_a$H$_b$); 8.32 (dd, 1H, J$_{8,7}$=8.3, J$_{8,6}$=1.3, H-8); 8.38 (s, 1H, H-2); 8.54 (dd, 1H, J$_{6,7}$=4.8, J$_{6,8}$=1.3, H-6); $^{13}$C NMR (125.7 MHz, DMSO-d$_6$): 62.00 (CH$_2$-5'); 70.58 (CH-3'); 71.29 (CH-2'); 85.86 (CH-4'); 86.93 (CH-1'); 94.99 (C-4a); 119.50 (CH-8); 119.55 (CH-7); 130.09 (C-8a); 140.38 (C-4b); 143.52 (CH-6); 155.81 (C-9a); 156.64 (CH-2); 158.26 (C-4); HR-ESI-MS: m/z (%): 318.1197 (100, [M+H]$^+$, calcd for C$_{14}$H$_{16}$O$_4$N$_5^+$: 318.1196); HR-ESI-MS: m/z (%): 340.1016 (100, [M+Na]$^+$, calcd for C$_{14}$H$_{15}$O$_4$N$_5$Na$^+$: 340.1016).

Example 17

4-Amino-9-(β-D-ribofuranosyl)-9H-pyrido[4',3':4,5]pyrrolo[2,3-d]pyrimidine (2c)

Compound 2c was prepared as described above for derivative 1c in example 16, from protected nucleoside 14 (300 mg, 0.46 mmol). After solvent was evaporated, product was crystallized from MeOH. Nucleoside 2c (75 mg, 51%) was obtained as a white powder.

$R_f$=0.35 (C-18; MeOH/H$_2$O 1:1); [α]$_D^{20}$=−58.8 (c=0.265 in DMSO); $^1$H NMR (500.0 MHz, DMSO-d$_6$): 3.67 (ddd, 1H, J$_{gem}$=11.9, J$_{5'b,OH}$=5.9, J$_{5'b,4'}$=3.5, H-5'b); 3.72 (ddd, 1H, J$_{gem}$=11.9, J$_{5'a,OH}$=4.8, J$_{5'a,4'}$=3.1, H-5'a); 3.98 (ddd, 1H, J$_{4',5'}$=3.5, 3.1, J$_{4',3'}$=2.7, H-4'); 4.20 (ddd, 1H, J$_{3',2'}$=5.8, J$_{3',OH}$=4.6, J$_{3',4'}$=2.7, H-3'); 4.72 (ddd, 1H, J$_{2',1'}$=7.5, J$_{2',OH}$=6.8, J$_{2',3'}$=5.7, H-2'); 5.17 (d, 1H, J$_{OH,3'}$=4.6, OH-3'); 5.22 (bd, 1H, J$_{OH,2'}$=6.8, OH-2'); 5.37 (dd, 1H, J$_{OH,5'}$=5.9, 4.8, OH-5'); 6.42 (d, 1H, J$_{1',2'}$=7.5, H-1'); 7.64 (bs, 2H, NH$_2$); 8.36 (dd, 1H, J$_{5,6}$=5.3, J$_{5,8}$=1.1, H-5); 8.38 (s, 1H, H-2); 8.45 (d, 1H, J$_{6,5}$=5.3, H-6); 9.22 (d, 1H, J$_{8,5}$=1.1, H-8); $^{13}$C NMR (125.7 MHz, DMSO-d$_6$): 61.85 (CH$_2$-5'); 70.33 (CH-3'); 71.25 (CH-2'); 85.76 (CH-4'); 86.85 (CH-1'); 94.54 (C-4a); 115.40 (CH-5); 126.10 (C-4b); 132.28 (C-8a); 134.54 (CH-8); 140.91 (CH-6); 156.17 (C-9a); 156.91 (CH-2); 158.81 (C-4); HR-ESI-MS: m/z (%): 318.1197 (100, [M+H]$^+$, calcd for C$_{14}$H$_{16}$O$_4$N$_5^+$: 318.1196); HR-ESI-MS: m/z (%): 340.1016 (100, [M+Na]$^+$, calcd for C$_{14}$H$_{15}$O$_4$N$_5$Na$^+$: 340.1016).

Example 18

4-Methyl-9-(2,3,5-tri-O-benzoyl-β-D-ribofuranosyl)-9H-pyrido[2',3':4,5]pyrrolo[2,3-d]pyrimidine (15d)

(Me)$_3$Al (1.25 mL, 2M in toluene) and Pd(PPh$_3$)$_4$ (97 mg, 0.08 mmol) were added to the solution of nucleoside 13 (542 mg, 0.84 mmol) in THF (25 mL), then the reaction mixture was stirred at 70° C. for 16 h. Solvent was evaporated and the crude reaction mixture was purified by reverse phase column chromatography (C-18, H$_2$O/MeOH 0→100%). Protected nucleoside 15d (362 mg, 69%) was obtained as a yellowish foam.

$R_f$=0.58 (SiO$_2$; petroleum ether/EtOAc 1:3); $^1$H NMR (500.0 MHz, DMSO-d$_6$): 3.06 (s, 3H, CH$_3$); 4.70 (dd, 1H, J$_{gem}$=12.3, J$_{5'b,4'}$=4.3, H-5'b); 4.84 (dd, 1H, J$_{gem}$=12.3, J$_{5'a,4'}$=3.2, H-5'a); 4.90 (ddd, 1H, J$_{4',3'}$=6.6, J$_{4',5'}$=4.3, 3.2, H-4'); 6.37 (t, 1H, J$_{3',2'}$=J$_{3',4'}$6.6, H-3'); 6.60 (dd, 1H, J$_{2',3'}$=6.6, J$_{2',1'}$=4.6, H-2'); 7.01 (d, 1H, J$_{1',2'}$=4.6, H-1'); 7.41 (m, 2H, H-m-Bz); 7.47-7.52 (m, 5H, H-7, H-m-Bz); 7.61, 7.67, 7.68 (3×m, 3×1H, H-p-Bz); 7.83, 7.93, 8.00 (3×m, 3×2H, H-o-Bz); 8.45 (dd, 1H, J$_{8,7}$=8.5, J$_{8,6}$=1.4, H-8); 8.70 (dd, 1H, J$_{6,7}$=4.7, J$_{6,8}$=1.4, H-6); 8.87 (s, 1H, H-2); $^{13}$C NMR (125.7 MHz, DMSO-d$_6$): 22.15 (CH$_3$); 63.24 (CH$_2$-5'); 70.37 (CH-3'); 72.44 (CH-2'); 78.80 (CH-4'); 85.98 (CH-1'); 111.78 (C-4a); 119.31 (CH-8); 121.95 (CH-7); 128.63, 128.84 (C-i-Bz); 128.94, 128.97, 129.01 (CH-m-Bz); 129.40, 129.52, 129.66 (C-i-Bz, CH-o-Bz); 132.29 (C-8a); 133.80, 134.14 (CH-p-Bz); 139.17 (C-4b); 144.95 (CH-6); 154.70 (C-9a); 155.33 (CH-2); 162.34 (C-4); 164.81, 165.03, 165.59 (CO-Bz); HR-ESI-MS: m/z (%): 629.2032 (100, [M+H]$^+$, calcd for C$_{36}$H$_{29}$O$_7$N$_4^+$: 629.2030); HR-ESI-MS: m/z (%): 651.1851 (100, [M+Na]$^+$, calcd for C$_{36}$H$_{28}$O$_7$N$_4$Na$^+$: 651.1850).

Example 19

4-Methyl-9-(2,3,5-tri-O-benzoyl-β-D-ribofuranosyl)-9H-pyrido[4',3':4,5]pyrrolo[2,3-d]pyrimidine (16d)

Nucleoside 16 was prepared as described above for derivative 15d in example 18, from chlorinated intermediate 14 (400 mg, 0.62 mmol). The reaction mixture was stirred at 70° C. for 16 h. The solvent was evaporated and the crude reaction mixture was purified by column chromatography (SiO$_2$, cyclohexane/EtOAc 0→100%). Protected nucleoside 16d (215 mg, 55%) was obtained as a yellow powder.

$R_f$=0.18 (SiO$_2$; petroleum ether/EtOAc 1:2); $^1$H NMR (500.0 MHz, DMSO-d$_6$): 2.97 (s, 3H, CH$_3$); 4.73 (dd, 1H, J$_{gem}$=12.3, J$_{5'b,4'}$=4.5, H-5'b); 4.83 (dd, 1H, J$_{gem}$=12.3, J$_{5'a,4'}$=3.2, H-5'a); 4.92 (ddd, 1H, J$_{4',3'}$=6.5, J$_{4',5'}$=4.5, 3.2, H-4'); 6.36 (t, 1H, J$_{3',2'}$=J$_{3',4'}$6.5, H-3'); 6.63 (dd, 1H, J$_{2',3'}$=6.5, J$_{2',1'}$4.7, H-2'); 7.09 (d, 1H, J$_{1',2'}$=4.7, H-1'); 7.41, 7.48, 7.50 (3×m, 3×2H, H-m-Bz); 7.61, 7.66, 7.68 (3×m, 3×1H, H-p-Bz); 7.83, 7.92, 8.01 (3×m, 3×2H, H-o-Bz); 8.20 (dd, 1H, J$_{5,6}$=5.2, J$_{5,8}$=0.9, H-5); 8.64 (d, 1H, J$_{6,5}$=5.2, H-6); 8.90 (s, 1H, H-2); 9.45 (d, 1H, J$_{8,5}$=0.9, H-8); $^{13}$C NMR (125.7 MHz, DMSO-d$_6$): 22.99 (CH$_3$); 63.29 (CH$_2$-5'); 70.40 (CH-3'); 72.42 (CH-2'); 78.89 (CH-4'); 86.12 (CH-1'); 111.54 (C-4a); 117.15 (CH-5); 125.62 (C-4b); 128.62, 128.83 (C-i-Bz); 128.90, 128.91, 128.99 (CH-m-Bz); 129.34 (C-i-Bz); 129.36, 129.50, 129.64 (CH-o-Bz); 133.74 (CH-p-Bz); 134.04 (C-8a); 134.11 (CH-p-Bz); 134.52 (CH-8); 142.32 (CH-6); 154.65 (C-9a); 156.10 (CH-2); 163.40 (C-4); 164.80, 165.03, 165.58 (CO-Bz); HR-ESI-MS: m/z (%): 629.2032 (100, [M+H]$^+$, calcd for C$_{36}$H$_{29}$O$_7$N$_4^+$: 629.2030); HR-ESI-MS: m/z (%): 651.1850 (100, [M+Na]$^+$, calcd for C$_{36}$H$_{28}$O$_7$N$_4$Na$^+$: 651.1850).

Example 20

4-Methyl-9-(β-D-ribofuranosyl)-9H-pyrido[2',3':4,5]pyrrolo[2,3-d]pyrimidine (1d)

To a suspension of nucleoside 15d (340 mg, 0.54 mmol) in MeOH (12 mL) and DMF (10 mL) mixture, sodium methoxide (37 μL, 25 wt. % in methanol, 0.16 mmol) was added. The reaction mixture was stirred for 16 h at 90° C., then the solvent was evaporated and the product was crystallized from MeOH:CHCl$_3$ mixture. Nucleoside 1d (149 mg, 87%) was obtained as a white powder.

$R_f$=0.60 (SiO$_2$; CHCl$_3$/MeOH 5:1); [α]$_D^{20}$=−33.3 (c=0.117 in DMSO); $^1$H NMR (500.0 MHz, DMSO-d$_6$):

3.08 (s, 3H, CH$_3$); 3.69 (ddd, 1H, J$_{gem}$=12.0, J$_{5'b,OH}$=5.5, J$_{5'b,4'}$=3.5, H-5'b); 3.73 (ddd, 1H, J$_{gem}$=12.0, J$_{5'a,OH}$=5.2, J$_{5'a,4'}$=3.2, H-5'a); 4.01 (ddd, 1H, J$_{4',5'}$=3.5, 3.2, J$_{4',3'}$=2.7, H-4'); 4.22 (ddd, 1H, J$_{3',2'}$=5.7, J$_{3',OH}$=4.5, J$_{3',4'}$=2.7, H-3'); 4.72 (ddd, 1H, J$_{2',1'}$=7.5, J$_{2',OH}$=6.3, J$_{2',3'}$=5.7, H-2'); 5.21 (d, 1H, J$_{OH,3'}$=4.5, OH-3'); 5.26 (dd, 1H, J$_{OH,5'}$=5.5, 5.2, OH-5'); 5.28 (bd, 1H, J$_{OH,2'}$=6.3, OH-2'); 6.52 (d, 1H, J$_{1',2'}$=7.5, H-1'); 7.55 (dd, 1H, J$_{7,8}$=8.4, J$_{7,6}$=4.7, H-7); 8.52 (dd, 1H, J$_{8,7}$=8.4, J$_{8,6}$=1.4, H-8); 8.69 (dd, 1H, J$_{6,7}$=4.7, J$_{6,8}$=1.4, H-6); 8.94 (s, 1H, H-2); $^{13}$C NMR (125.7 MHz, DMSO-d$_6$): 22.06 (CH$_3$); 61.75 (CH$_2$-5'); 70.32 (CH-3'); 71.05 (CH-2'); 85.82 (CH-4'); 86.72 (CH-1'); 111.25 (C-4a); 120.71 (CH-8); 121.69 (CH-7); 131.77 (C-8a); 139.41 (C-4b); 144.43 (CH-6); 155.26 (C-9a); 155.27 (CH-2); 161.91 (C-4); HR-ESI-MS: m/z (%): 317.1244 (100, [M+H]$^+$, calcd for C$_{15}$H$_{17}$O$_4$N$_4^+$: 317.1244); HR-ESI-MS: m/z (%): 339.1064 (100, [M+Na]$^+$, calcd for C$_{15}$H$_{16}$O$_4$N$_4$Na$^+$: 339.1063).

Example 21

4-Methyl-9-β-ribofuranosyl)-9H-pyrido[4',3':4,5]pyrrolo[2,3-d]pyrimidine (2d)

To a suspension of nucleoside 16d (218 mg, 0.35 mmol) in MeOH (7.7 mL) was added sodium methoxide (24 μL, 25 wt. % in methanol, 0.11 mmol). The reaction mixture was stirred for 16 h at 22° C., then the solvent was evaporated and the crude material was purified using reverse phase column chromatography (C-18, water/MeOH 0→100%). Nucleoside 2d (69 mg, 63%) was obtained as a white powder.

R$_f$=0.20 (SiO$_2$; CHCl$_3$/MeOH 10:1); [α]$_D^{20}$=−49.5 (c=0.196 in DMSO); $^1$H NMR (500.0 MHz, DMSO-d$_6$): 2.99 (s, 3H, CH$_3$); 3.71, 3.74 (2×ddd, 2×1H, J$_{gem}$=11.9, J$_{5',OH}$=5.1, J$_{5',4'}$=3.4, H-5'); 4.02 (td, 1H, J$_{4',5'}$=3.4, J$_{4',3'}$=2.7, H-4'); 4.24 (ddd, 1H, J$_{3',2'}$=5.8, J$_{3',OH}$=4.2, J$_{3',4'}$=2.7, H-3'); 4.73 (dt, 1H, J$_{2',1'}$=7.5, J$_{2',3'}$=J$_{2',OH}$=5.8, H-2'); 5.24 (d, 1H, J$_{OH,3'}$=4.2, OH-3'); 5.26 (t, 1H, J$_{OH,5'}$=5.1, OH-5'); 5.29 (d, 1H, J$_{OH,2'}$=5.8, OH-2'); 6.55 (d, 1H, J$_{1',2'}$=7.5, H-1'); 8.21 (dd, 1H, J$_{5,6}$=5.3, J$_{5,8}$=1.1, H-5); 8.61 (d, 1H, J$_{6,5}$=5.3, H-6); 8.98 (s, 1H, H-2); 9.48 (d, 1H, J$_{8,5}$=1.1, H-8); $^{13}$C NMR (125.7 MHz, DMSO-d$_6$): 22.93 (CH$_3$); 61.67 (CH$_2$-5'); 70.20 (CH-3'); 71.25 (CH-2'); 85.90 (CH-4'); 86.70 (CH-1'); 110.94 (C-4a); 116.95 (CH-5); 125.75 (C-4b); 133.52 (C-8a); 136.04 (CH-8); 141.65 (CH-6); 155.27 (C-9a); 156.11 (CH-2); 162.92 (C-4); HR-ESI-MS: m/z (%): 317.1246 (100, [M+H]$^+$, calcd for C$_{15}$H$_{17}$O$_4$N$_4^+$: 317.1244); HR-ESI-MS: m/z (%): 339.1063 (100, [M+Na]$^+$, calcd for C$_{15}$H$_{16}$O$_4$N$_4$Na$^+$: 339.1063).

Example 22

4-(Dimethylamino)-9-(2,3,5-tri-O-benzoyl-β-D-ribofuranosyl)-9H-pyrido[2',3':4,5] pyrrolo[2,3-d]pyrimidine (15e)

To the solution of nucleoside 13 (593 mg, 0.91 mmol) in the mixture of isopropanol (20 mL) and dichloromethane (7 mL), dimethylamine (1.36 mL, 2M in THF, 2.73 mmol) was added in one portion. The reaction mixture was stirred at 22° C. for 16 h. Solvent was evaporated and the crude material was purified by column chromatography (SiO$_2$, petroleum ether/EtOAc 0→50%). Protected nucleoside 15e (495 mg, 82%) was obtained as a white powder.

R$_f$=0.68 (SiO$_2$; petroleum ether/EtOAc 3:2); $^1$H NMR (500.0 MHz, DMSO-d$_6$): 3.60 (bs, 6H, (CH$_3$)$_2$N); 4.70 (dd, 1H, J$_{gem}$=12.3, J$_{5'b,4'}$=4.4, H-5'b); 4.82 (dd, 1H, J$_{gem}$=12.3, J$_{5'a,4'}$=3.2, H-5'b); 4.87 (dd, 1H, J$_{4',3'}$=6.6, J$_{4',5'}$=4.4, 3.2, H-4'); 6.35 (t, 1H, J$_{3',2'}$=J$_{3',4'}$=6.6, H-3'); 6.55 (dd, 1H, J$_{2',3'}$=6.6, J$_{2',1'}$=4.7, H-2'); 6.97 (d, 1H, J$_{1',2'}$=4.7, H-1'); 7.27 (dd, 1H, J$_{7,8}$=8.3, J$_{7,6}$=4.7, H-7); 7.42, 7.49, 7.51 (3×m, 3×2H, H-m-Bz); 7.62, 7.68, 7.69 (3×m, 3×1H, H-p-Bz); 7.84, 7.97, 7.99 (3×m, 3×2H, H-o-Bz); 8.30 (dd, 1H, J$_{8,7}$=8.4, H$_{8,6}$=1.4, H-8); 8.39 (s, 1H, H-2); 8.55 (dd, 1H, J$_{6,7}$=4.7, J$_{6,8}$=1.4, H-6); $^{13}$C NMR (125.7 MHz, DMSO-d$_6$): 40.12 ((CH$_3$)$_2$N); 63.40 (CH$_2$-5'); 70.46 (CH-3'); 72.37 (CH-2'); 78.62 (CH-4'); 85.91 (CH-1'); 96.39 (C-4a); 118.16 (CH-8); 119.26 (CH-7); 128.66, 128.85 (C-i-Bz); 128.90, 128.97 (CH-m-Bz); 129.43 (C-i-Bz); 129.43, 129.49, 129.60 (CH-o-Bz); 130.08 (C-8a); 133.77, 134.08 (CH-p-Bz); 139.40 (C-4b); 143.24 (CH-6); 154.87 (CH-2); 156.79 (C-9a); 158.76 (C-4); 164.80, 165.02, 165.62 (CO-Bz); HR-ESI-MS: m/z (%): 658.2300 (100, [M+H]$^+$, calcd for C$_{37}$H$_{32}$O$_7$N$_5^+$: 658.2296); HR-ESI-MS: m/z (%): 680.2118 (100, [M+Na]$^+$, calcd for C$_{37}$H$_{31}$O$_7$N$_5$Na$^+$: 680.2115).

Example 23

4-(Dimethylamino)-9-(2,3,5-tri-O-benzoyl-β-D-ribofuranosyl)-pyrido[4',3':4,5]pyrrolo[2,3-d]pyrimidine (16e)

Protected nucleoside 16e was prepared as described above for derivative 15e in example 22, from chlorinated intermediate 14 (500 mg, 0.77 mmol). After solvent was evaporated, the crude mixture was purified by column chromatography (SiO$_2$, cyclohexane/EtOAc 0→80%). Protected nucleoside 16e (339 mg, 67%) was obtained as a white powder.

R$_f$=0.16 (SiO$_2$; petroleum ether/EtOAc 1:2); $^1$H NMR (500.0 MHz, DMSO-d$_6$): 3.33 (s, 3H, CH$_3$N, overlapped with H$_2$O signal); 4.72 (dd, 1H, J$_{gem}$=12.3, J$_{5'b,4'}$4.7, H-5'b); 4.80 (dd, 1H, J$_{gem}$=12.3, J$_{5'a,4'}$=3.2, H-5'a); 4.88 (ddd, 1H, J$_{4'3'}$=6.6, J$_{4',5'}$=4.7, 3.2, H-4'); 6.35 (t, 1H, J$_{3',2'}$=J$_{3',4'}$=6.6, H-3'); 6.61 (dd, 1H, J$_{2',3'}$=6.6, J$_{2',1'}$=4.7, H-2'); 7.04 (d, 1H, J$_{1',2'}$=4.7, H-1'); 7.41, 7.48, 7.49 (3×m, 3×2H, H-m-Bz); 7.61, 7.66, 7.67 (3×m, 3×1H, H-p-Bz); 7.84 (m, 2H, H-o-Bz); 7.93 (dd, 1H, J$_{5,6}$=5.5, J$_{5,8}$=1.0, H-5); 7.95, 7.99 (2×m, 2×2H, H-o-Bz); 8.43 (s, 1H, H-2); 8.47 (d, 1H, J$_{6,5}$=5.5, H-6); 9.30 (d, 1H, J$_{8,5}$=1.0, H-8); $^{13}$C NMR (125.7 MHz, DMSO-d$_6$): 40.04 (CH$_3$N); 63.44 (CH$_2$-5'); 70.46 (CH-3'); 72.41 (CH-2'); 78.69 (CH-4'); 86.03 (CH-1'); 96.26 (C-4a); 117.08 (CH-5); 126.15 (C-4b); 128.67, 128.83 (C-i-Bz); 128.88, 128.91, 128.95 (CH-m-Bz); 129.36 (C-i-Bz); 129.39, 129.49, 129.59 (CH-o-Bz); 132.75 (C-8a); 133.67 (CH-8); 133.70, 134.05 (CH-p-Bz); 141.59 (CH-6); 155.41 (CH-2); 156.71 (C-9a); 160.16 (C-4); 164.79, 164.99, 165.60 (CO-Bz);); HR-ESI-MS: m/z (%): 658.2298 (100, [M+H]$^+$, calcd for C$_{37}$H$_{32}$O$_7$N$_5^+$: 658.2296); HR-ESI-MS: m/z (%): 680.2117 (100, [M+Na]$^+$, calcd for C$_{37}$H$_{31}$O$_7$N$_5$Na$^+$: 680.2115).

Example 24

4-(Dimethylamino)-9-(β-D-ribofuranosyl)-9H-pyrido[2',3':4,5]pyrrolo[2,3-d]pyrimidine (1e)

To a suspension of nucleoside 15e (320 mg, 0.49 mmol) in MeOH (12 mL) was added sodium methoxide (34 μL, 25 wt. % in methanol, 0.15 mmol). The reaction mixture was stirred for 16 h at 22° C., then the solvent was evaporated and the crude material was purified using reverse phase column chromatography (C-18, water/MeOH 0→100%). Nucleoside 1e (136 mg, 81%) was obtained as a white powder.

$R_f$=0.72 (SiO$_2$; CHCl$_3$/MeOH 5:1); $[\alpha]_D^{20}$=+10.8 (c=0.259 in DMSO); $^1$H NMR (500.0 MHz, DMSO-d$_6$): 3.62 (bs, 6H, (CH$_3$)$_2$N); 3.65-3.74 (m, 2H, H-5'); 3.98 (td, 1H, $J_{4',5'}$=3.3, $J_{4',3'}$=2.8, H-4'); 4.20 (dd, 1H, $J_{3',2'}$=5.8, $J_{3',4'}$=2.8, H-3'); 4.71 (dd, 1H, $J_{2',1'}$=7.5, $J_{2',3'}$=5.8, H-2'); 5.22 (bs, 2H, OH-2',3'); 5.36 (bs, 1H, OH-5'); 6.50 (d, 1H, $J_{1',2'}$=7.5, H-1'); 7.37 (dd, 1H, $J_{7,8}$=8.3, $J_{7,6}$=4.7, H-7); 8.35 (dd, 1H, $J_{8,7}$=8.3, $J_{8,6}$=1.4, H-8); 8.41 (s, 1H, H-2); 8.54 (dd, 1H, $J_{6,7}$=4.7, $J_{6,8}$=1.4, H-6); $^{13}$C NMR (125.7 MHz, DMSO-d$_6$): 40.13 ((CH$_3$)$_2$N); 61.86 (CH$_2$-5'); 70.34 (CH-3'); 70.94 (CH-2'); 85.66 (CH-4'); 86.86 (CH-1'); 96.06 (C-4a); 119.11 (CH-7); 119.43 (CH-8); 129.82 (C-8a); 139.44 (C-4b); 142.72 (CH-6); 154.66 (CH-2); 157.17 (C-9a); 158.86 (C-4); HR-ESI-MS: m/z (%): 346.1510 (100, [M+H]$^+$, calcd for C$_{16}$H$_{20}$O$_4$N$_5^+$: 346.1509); HR-ESI-MS: m/z (%): 368.1329 (100, [M+Na]$^+$, calcd for C$_{16}$H$_{19}$O$_4$N$_5$Na$^+$: 368.1329).

Example 25

4-(Dimethylamino)-9-(β-D-ribofuranosyl)-pyrido[4', 3':4,5]pyrrolo[2,3-d]pyrimidine (2e)

Nucleoside 2e was prepared as described above for derivative 1e in example 24, from protectednucleoside 16e (292 mg, 0.44 mmol). The crude material was purified using reverse phase column chromatography (C-18, water/MeOH 0→100%). Nucleoside 2e (140 mg, 91%) was obtained as a white powder.

$R_f$=0.14 (SiO$_2$; CHCl$_3$/MeOH 10:1); $[\alpha]_D^{20}$=−13.8 (c=0.246 in DMSO); $^1$H NMR (500.0 MHz, DMSO-d$_6$): 3.33 (s, 6H, CH$_3$N, overlapped with H$_2$O signal); 3.68, 3.72 (2×bddd, 2×1H, $J_{gem}$=11.9, $J_{5',OH}$=5.1, $J_{5'4}$=3.4, H-5'); 3.99 (td, 1H, $J_{4',5'}$=3.4, $J_{4',3'}$=2.8, H-4'); 4.22 (dd, 1H, $J_{3',2'}$=5.8, $J_{3',4'}$=2.8, H-3'); 4.73 (dd, 1H, $J_{2',1'}$=7.6, $J_{2',3'}$=5.8, H-2'); 5.21, 5.24 (2×bs, 2×1H, OH-2',3'); 5.32 (bt, 1H, $J_{OH,5}$=5.1, OH-5'); 6.51 (d, 1H, $J_{1',2'}$=7.6, H-1'); 7.92 (dd, 1H, $J_{5,6}$=5.5, $J_{5,8}$=1.0, H-5); 8.44 (d, 1H, $J_{6,5}$=5.5, H-6); 8.47 (s, 1H, H-2); 9.28 (d, 1H, $J_{8,5}$=1.0, H-8); $^{13}$C NMR (125.7 MHz, DMSO-d$_6$): 39.96 (CH$_3$N); 61.78 (CH$_2$-5'); 70.21 (CH-3'); 71.20 (CH-2'); 85.74 (CH-4'); 86.88 (CH-1'); 95.92 (C-4a); 116.92 (CH-5); 126.11 (C-4b); 132.40 (C-8a); 135.05 (CH-8); 140.93 (CH-6); 155.33 (CH-7); 157.19 (C-9a); 160.32 (C-4); HR-ESI-MS: m/z (%): 346.1510 (100, [M+H]$^+$, calcd for C$_{16}$H$_{20}$O$_4$N$_5^+$: 346.1509); HR-ESI-MS: m/z (%): 368.1329 (100, [M+Na]$^+$, calcd for C$_{16}$H$_{19}$O$_4$N$_5$Na$^+$: 368.1329).

Example 26

4-(Furan-2-yl)-9-(2,3,5-tri-O-benzoyl-β-D-ribofuranosyl)-9H-pyrido[2',3':4,5]pyrrolo[2,3-d]pyrimidine (15f)

Protected nucleoside 15f was prepared according to the general procedure A. Chlorinated intermediate 13 (400 mg, 0.62 mmol), 2-(tributylstannyl)furan (292 µl, 0.93 mmol) and PdCl$_2$(PPh$_3$)$_2$ (44 mg, 0.06 mmol) were used. Desired nucleoside 15f (378 mg, 90%) was obtained as a pinkish solid.

$R_f$=0.32 (SiO$_2$; petroleum ether/EtOAc 2:1); $^1$H NMR (500.0 MHz, DMSO-d$_6$): 4.73 (dd, 1H, $J_{gem}$=12.3, $J_{5'b,4'}$=4.4, H-5'b); 4.86 (dd, 1H, $J_{gem}$=12.3, $J_{5'a,4'}$=3.2, H-5'a); 4.92 (ddd, 1H, $J_{4',3'}$=6.6, $J_{4',5'}$=4.4, 3.2, H-4'); 6.40 (t, 1H, $J_{3',2'}$=$J_{3',4'}$=6.6, H-3'); 6.58 (dd, 1H, $J_{2',3}$=6.6, $J_{2',1'}$=4.6, H-2'); 6.91 (dd, 2H, $J_{4,3}$=3.6, $J_{4,5}$=1.7, H-4-furyl); 7.08 (d, 1H, $J_{1',2'}$=4.6, H-1'); 7.41, 7.49, 7.50 (3×m, 3×2H, H-m-Bz); 7.56 (dd, 1H, $J_{7,8}$=8.4, $J_{7,6}$=4.7, H-7); 7.62, 7.66, 7.69 (3×m, 3×1H, H-p-Bz); 7.83, 7.95, 8.00 (3×m, 3×2H, H-o-Bz); 8.12 (dd, 1H, $J_{5,4}$=1.7, $J_{5,3}$=0.8, H-5-furyl); 8.53 (dd, 1H, $J_{8,7}$=8.4, $J_{8,6}$=1.4, H-8); 8.81 (dd, 1H, $J_{6,7}$=4.7, $J_{6,8}$=1.4, H-6); 9.00 (s, 1H, H-2); 9.41 (dd, 1H, $J_{3,4}$=3.6, $J_{3,5}$=0.8, H-3-furyl); $^{13}$C NMR (125.7 MHz, DMSO-d$_6$): 63.25 (CH$_2$-5'); 70.33 (CH-3'); 72.51 (CH-2'); 78.80 (CH-4'); 86.03 (CH-1'); 106.95 (C-4a); 113.14 (CH-4-furyl); 119.36 (CH-8); 120.59 (CH-3-furyl); 122.23 (CH-7); 128.63, 128.83 (C-i-Bz); 128.88, 128.94, 128.97 (CH-m-Bz); 129.37 (CH-o-Bz); 129.39 (C-i-Bz); 129.48, 129.61 (CH-o-Bz); 132.44 (C-8a); 133.75, 134.08 (CH-p-Bz); 137.68 (C-4b); 144.45 (CH-6); 147.06 (CH-5-furyl); 148.91 (C-4); 150.38 (C-2-furyl); 155.31 (CH-2); 155.92 (C-9a); 164.80, 165.00, 165.58 (CO-Bz); HR-ESI-MS: m/z (%): 681.1982 (100, [M+H]$^+$, calcd for C$_{39}$H$_{29}$O$_8$N$_4^+$: 681.1979); HR-ESI-MS: m/z (%): 703.1800 (100, [M+H]$^+$, calcd for C$_{39}$H$_{29}$O$_8$N$_4$Na$^+$: 703.1799).

Example 27

4-(Furan-2-yl)-9-(2,3,5-tri-O-benzoyl-β-D-ribofuranosyl)-9H-pyrido[4',3':4,5]pyrrolo[2,3-d]pyrimidine (16f)

Protected nucleoside 15f was prepared according to the general procedure A. Protected nucleoside 14 (400 mg, 0.62 mmol), 2-(tributylstannyl)furan (292 µl, 0.93 mmol) and PdCl$_2$(PPh$_3$)$_2$ (44 mg, 0.06 mmol) were used. Desired nucleoside 16f (274 mg, 66%) was obtained as a pinkish solid.

$R_f$=0.41 (SiO$_2$; petroleum ether/EtOAc 1:2); $^1$H NMR (500.0 MHz, DMSO-d$_6$): 4.75 (dd, 1H, $J_{gem}$=12.3, $J_{5'b,4'}$=4.7, H-5'b); 4.85 (dd, 1H, $J_{gem}$=12.3, $J_{5'a,4'}$=3.2, H-5'a); 4.93 (ddd, 1H, $J_{4',3'}$=6.6, $J_{4',5'}$=4.7, 3.2, H-4'); 6.38 (t, 1H, $J_{3',2'}$=$J_{3',4'}$=6.6, H-3'); 6.62 (dd, 1H, $J_{2',3}$=6.6, $J_{2',1'}$=4.6, H-2'); 6.93 (dd, 1H, $J_{4,3}$=3.5, $J_{4,5}$=1.7, H-4-furyl); 7.15 (d, 1H, $J_{1',2'}$=4.6, H-1'); 7.41, 7.47, 7.51 (3×m, 3×2H, H-m-Bz); 7.62, 7.63 (2×m, 2×1H, H-p-Bz); 7.68 (dd, 1H, $J_{3,4}$=3.5, $J_{3,5}$=0.9, H-3-furyl); 7.69 (m, 1H, H-p-Bz); 7.84, 7.93, 8.01 (3×m, 3×2H, H-o-Bz); 8.37 (dd, 1H, $J_{5,4}$=1.7, $J_{5,3}$=0.9, H-5-furyl); 8.66 (d, 1H, $J_{6,5}$=5.4, H-6); 8.80 (dd, 1H, $J_{5,6}$=5.4, $J_{5,8}$=1.0, H-5); 9.00 (s, 1H, H-2); 9.48 (d, 1H, $J_{8,5}$=1.0, H-8); $^{13}$C NMR (125.7 MHz, DMSO-d$_6$): 63.34 (CH$_2$-5'); 70.37 (CH-3'); 72.45 (CH-2'); 78.89 (CH-4'); 86.11 (CH-1'); 106.75 (C-4a); 113.41 (CH-4-furyl); 116.28 (CH-3-furyl); 118.43 (CH-5); 125.05 (C-4b); 128.65, 128.82 (C-i-Bz); 128.87, 128.88, 128.96 (CH-m-Bz); 129.32 (C-i-Bz); 129.34, 129.49 129.61 (CH-o-Bz); 133.69, 134.07 (CH-p-Bz); 134.44 (C-8a); 134.61 (CH-8); 142.60 (CH-6); 147.70 (CH-5-furyl); 149.82 (C-4); 151.89 (C-2-furyl); 155.95 (CH-2); 156.31 (C-9a); 164.81, 164.99, 165.57 (CO-Bz); HR-ESI-MS: m/z (%): 681.1982 (100, [M+H]$^+$, calcd for C$_{39}$H$_{29}$O$_8$N$_4^+$: 681.1979); HR-ESI-MS: m/z (%): 703.1800 (100, [M+H]$^+$, calcd for C$_{39}$H$_{28}$O$_8$N$_4$Na$^+$: 703.1799).

Example 28

4-(Furan-2-yl)-9-(β-D-ribofuranosyl)-9H-pyrido[2', 3'4,5]pyrrolo[2,3-d]pyrimidine (1f)

To a suspension of nucleoside 15f (300 mg, 0.44 mmol) in MeOH (14 mL) was added sodium methoxide (30 µL, 25 wt. % in methanol, 0.13 mmol). The reaction mixture was stirred for 16 h at 70° C., then solvent was evaporated and the crude material was purified using reverse phase column chromatography (C-18, water/MeOH 0→100%). Nucleoside 1f (122 mg, 75%) was obtained as a white solid.

$R_f$=0.39 (SiO$_2$; CHCl$_3$/MeOH 10:1); $[α]_D^{20}$=−27.8 (c=0.212 in DMSO); $^1$H NMR (500.0 MHz, DMSO-d$_6$): 3.72 (ddd, 1H, $J_{gem}$=12.0, $J_{5'b,OH}$=5.3, $J_{5'b,4'}$=3.5, H-5'b); 3.75 (ddd, 1H, $J_{gem}$=12.0, $J_{5'a,OH}$=5.0, $J_{5'a,4'}$=3.1, H-5'b); 4.03 (ddd, 1H, $J_{4',5'}$=3.5, 3.1 $J_{4',3'}$=2.7, H-4'); 4.24 (ddd, 1H, $J_{3',2'}$=5.6, $J_{3',OH}$=4.5, $J_{3',4'}$=2.7, H-3'); 4.72 (ddd, 1H, $J_{2',1'}$=7.5, $J_{2',OH}$=5.6, H-2'); 5.23 (d, 1H, $J_{OH,3'}$=4.6, OH-3'); 5.28 (dd, 1H, $J_{OH,5'}$=5.3, 5.0, OH-5'); 5.31 (d, 1H, $J_{OH,2'}$=6.3, OH-2'); 6.63 (d, 1H, $J_{1',2'}$=7.5, H-1'); 6.91 (dd, 1H, $J_{4,3}$=3.5, $J_{4,5}$=1.7, H-4-furyl); 7.63 (dd, 1H, $J_{7,8}$=8.4, $J_{7,6}$=4.7, H-7); 8.11 (dd, 1H, $J_{5,4}$=1.7, $J_{5,3}$=0.8, H-5-furyl); 8.63 (dd, 1H, $J_{8,7}$=8.4, $J_{8,6}$=1.4, H-8); 8.80 (dd, 1H, $J_{6,7}$=4.7, $J_{6,8}$=1.4, H-6); 9.07 (s, 1H, H-2); 9.44 (dd, 1H, $J_{3,4}$=3.5, $J_{3,5}$=0.8, H-3-furyl); $^{13}$C NMR (125.7 MHz, DMSO-d$_6$): 61.71 (CH$_2$-5'); 70.26 (CH-3'); 71.02 (CH-2'); 85.87 (CH-4'); 86.74 (CH-1'); 106.48 (C-4a); 113.07 (CH-4-furyl); 120.33 (CH-3-furyl); 120.90 (CH-8); 122.02 (CH-7); 131.95 (C-8a); 137.88 (C-4b); 143.98 (CH-6); 146.86 (CH-5-furyl); 148.71 (C-4); 150.54 (C-2-furyl); 155.31 (CH-2); 156.51 (C-9a); HR-ESI-MS: m/z (%): 369.1194 (100, [M+H]$^+$, calcd for C$_{18}$H$_{17}$O$_5$N$_4^+$: 369.1193); HR-ESI-MS: m/z (%): 391.1014 (100, [M+Na]$^+$, calcd for C$_{18}$H$_{16}$O$_5$N$_4$Na$^+$: 391.1012).

Example 29

4-(Furan-2-yl)-9-(β-D-ribofuranosyl)-9H-pyrido[4',3':4,5]pyrrolo[2,3-d]pyrimidine (2f)

To a suspension of nucleoside 16f (230 mg, 0.34 mmol) in a mixture of MeOH (9 mL) and DMF (4.5 mL) was added sodium methoxide (22 μL, 25 wt. % in methanol, 0.10 mmol). The reaction mixture was stirred for 16 h at 60° C., then solvent was evaporated and the crude material was purified using column chromatography (CHCl$_3$/MeOH 0→10%). Nucleoside 2f (88 mg, 71%) was obtained as a pinkish solid.

$R_f$=0.19 (SiO$_2$; CHCl$_3$/MeOH 10:1); $[α]_D^{20}$=−43.3 (c=0.247 in DMSO); $^1$H NMR (500.0 MHz, DMSO-d$_6$): 3.73 (ddd, 1H, $J_{gem}$=11.9, $J_{5'b,OH}$=5.1, $J_{5'b,4'}$=3.5, H-5'b); 3.76 (ddd, 1H, $J_{gem}$=11.9, $J_{5'a,OH}$=5.1, $J_{5'a,4'}$=3.2, H-5'a); 4.04 (ddd, 1H, $J_{4',5'}$=3.5, 3.2, $J_{4',3'}$=2.8, H-4'); 4.26 (ddd, 1H, $J_{3',2'}$=5.8, $J_{3',OH}$=4.6, $J_{3',4'}$=2.8, H-3'); 4.75 (ddd, 1H, $J_{2',1'}$=7.6, $J_{2',OH}$=6.3, $J_{2',3'}$=5.8, H-2'); 5.24 (d, 1H, $J_{OH,3'}$=4.6, OH-3'); 5.27 (t, 1H, $J_{OH,5'}$=5.1, OH-5'); 5.31 (d, 1H, $J_{OH,2'}$=6.3, OH-2'); 6.64 (d, 1H, $J_{1',2'}$=7.6, H-1'); 6.92 (dd, 1H, $J_{4,3}$=3.5, $J_{4,5}$=1.8, H-4-furyl); 7.67 (dd, 1H, $J_{3,4}$=3.5, $J_{3,5}$=0.9, H-3-furyl); 8.36 (dd, 1H, $J_{5,4}$=1.8, $J_{5,3}$=0.9, H-5-furyl); 8.63 (d, 1H, $J_{6,5}$=5.4, H-6); 8.80 (dd, 1H, $J_{5,6}$=5.4, $J_{5,8}$=1.1, H-5); 9.07 (s, 1H, H-2); 9.52 (d, 1H, $J_{8,5}$=1.1, H-8); $^{13}$C NMR (125.7 MHz, DMSO-d$_6$): 61.62 (CH$_2$-5'); 70.12 (CH-3'); 71.12 (CH-2'); 85.92 (CH-4'); 86.73 (CH-1'); 106.25 (C-4a); 113.35 (CH-4-furyl); 116.01 (CH-3-furyl); 118.27 (CH-5); 125.16 (C-4b); 133.96 (C-8a); 136.21 (CH-8); 141.96 (CH-6); 147.49 (CH-5-furyl); 149.60 (C-4); 152.06 (C-2-furyl); 156.03 (CH-2); 156.95 (C-9a); HR-ESI-MS: m/z (%): 369.1194 (100, [M+H]$^+$, calcd for C$_{18}$H$_{17}$O$_5$N$_4^+$: 369.1193); HR-ESI-MS: m/z (%): 391.1013 (100, [M+Na]$^+$, calcd for C$_{18}$H$_{16}$O$_5$N$_4$Na$^+$: 391.1012).

Example 30

4-(Furan-3-yl)-9-(2,3,5-tri-O-benzoyl-β-D-ribofuranosyl)-9H-pyrido[2',3':4,5]pyrrolo[2,3-d]pyrimidine (15g)

Protected nucleoside 13 (400 mg, 0.62 mmol), furan-3-ylboronic acid (105 mg, 0.93 mmol), K$_2$CO$_3$ (171 mg, 1.24 mmol) and Pd(PPh$_3$)$_4$ (35 mg, 0.03 mmol) were dissolved in toluene (13.5 mL) and heated to 100° C. for 24 h. Then, the reaction mixture was diluted with saturated solution of NaHCO$_3$ and extracted with EtOAc. Organic layer was dried over Na$_2$SO$_4$. After evaporation of solvent, the crude product was purified by column chromatography (SiO$_2$, petroleum ether/EtOAc 0→100%). Protected nucleoside 15g (308 mg, 73%) was obtained as a white solid.

$R_f$=0.74 (SO$_2$; petroleum ether/EtOAc 2:1); $^1$H NMR (500.0 MHz, DMSO-d$_6$): 4.73 (dd, 1H, $J_{gem}$=12.3, $J_{5'b,4'}$=4.4, H-5'b); 4.86 (dd, 1H, $J_{gem}$=12.3, $J_{5'a,4'}$=3.2, H-5'b); 4.92 (ddd, 1H, $J_{4',3'}$=6.6, $J_{4',5'}$=4.4, 3.2, H-4'); 6.39 (t, 1H, $J_{3',2'}$=$J_{3',4'}$=6.6, H-3'); 6.60 (dd, 1H, $J_{2',3'}$=6.6, $J_{2',1'}$=4.7, H-2'); 7.08 (d, 1H, $J_{1',2'}$=4.7, H-1'); 7.41, 7.49, 7.50 (3×m, 3×2H, H-m-Bz); 7.55 (dd, 1H, $J_{7,8}$=8.4, $J_{7,6}$=4.7, H-7); 7.61, 7.66 (2×m, 2×1H, H-p-Bz); 7.67 (dd, 1H, $J_{4,5}$=2.3, $J_{4,2}$=0.8, H-4-furyl); 7.68 (m, 1H, H-Bz); 7.83 (m, 2H, H-o-Bz); 7.94 (dd, 1H, $J_{5,4}$=2.3, $J_{5,2}$=1.5, H-5-furyl); 7.95, 8.00 (2×m, 2×2H, H-o-Bz); 8.53 (dd, 1H, $J_{8,7}$=8.4, $J_{8,6}$=1.4, H-8); 8.80 (dd, 1H, $J_{6,7}$=4.7, $J_{6,8}$=1.4, H-6); 9.01 (s, 1H, H-2); 10.01 (dd, 1H, $J_{2,5}$=1.5, $J_{2,4}$=0.8, H-2-furyl); $^{13}$C NMR (125.7 MHz, DMSO-d$_6$): 63.30 (CH$_2$-5'); 70.38 (CH-3'); 72.46 (CH-2'); 78.82 (CH-4'); 86.05 (CH-1'); 108.97 (C-4a); 110.43 (CH-4-furyl); 119.43 (CH-8); 122.11 (CH-7); 125.30 (C-3-furyl); 128.63, 128.83 (C-i-Bz); 128.89, 128.94, 128.97 (CH-m-Bz); 129.37 (CH-o-Bz); 129.39 (C-i-Bz); 129.48, 129.62 (CH-o-Bz); 132.38 (C-8a); 133.76, 134.09 (CH-p-Bz); 138.07 (C-4b); 144.29 (CH-5-furyl); 144.45 (CH-6); 149.52 (CH-2-furyl); 152.83 (C-4); 155.45 (CH-2); 155.88 (C-9a); 164.81, 165.01, 165.59 (CO-Bz); HR-ESI-MS: m/z (%): 703.1802 (100, [M+Na]$^+$, calcd for C$_{39}$H$_{28}$O$_8$N$_4$Na$^+$: 703.1799).

Example 31

4-(Furan-3-yl)-9-(2,3,5-tri-O-benzoyl-β-D-ribofuranosyl)-9H-pyrido[4',3':4,5]pyrrolo[2,3-d]pyrimidine (16g)

Protected nucleoside 14 (500 mg, 0.77 mmol), furan-3-ylboronic acid (259 mg, 2.31 mmol), K$_2$CO$_3$ (213 mg, 1.54 mmol) and Pd(PPh$_3$)$_4$ (46 mg, 0.04 mmol) were dissolved in toluene (17 mL) and heated to 100° C. for 4 hours. Then, the reaction mixture was diluted with saturated solution of NaHCO$_3$ and extracted with EtOAc. Organic layer was dried over Na$_2$SO$_4$. After evaporation of solvent, the crude product was purified by column chromatography (SiO$_2$, petroleum ether/EtOAc 0→100%). Protected nucleoside 16g (443 mg, 84%) was obtained as a white solid.

$R_f$=0.48 (SiO$_2$; petroleum ether/EtOAc 1:2); $^1$H NMR (500.0 MHz, DMSO-d$_6$): 4.75 (dd, 1H, $J_{gem}$=12.3, $J_{5'b,4'}$=4.6, H-5'b); 4.85 (dd, 1H, $J_{gem}$=12.3, $J_{5'a,4'}$=3.2, H-5'a); 4.94 (ddd, 1H, $J_{4',3'}$=6.5, $J_{4',5'}$=4.5, 3.2, H-4'); 6.39 (t, 1H, $J_{3',2'}$=$J_{3',4'}$=6.5, H-3'); 6.65 (dd, 1H, $J_{2',3'}$=6.5, $J_{2',1'}$=4.7, H-2'); 7.15 (d, 1H, $J_{1',2'}$=4.7, H-1'); 7.17 (dd, 1H, $J_{4,5}$=1.9, $J_{4,2}$=0.9, H-4-furyl); 7.42, 7.48, 7.51 (3×m, 3×2H, H-m-Bz); 7.62, 7.65, 7.69 (3×m, 3×1H, H-p-Bz); 7.85, 7.94, 8.01 (3×m, 3×2H, H-o-Bz); 8.02 (dd, 1H, $J_{5,4}$=1.9, $J_{5,2}$=1.5, H-5-furyl); 8.15 (dd, 1H, $J_{5,6}$=5.4, $J_{5,8}$=1.0, H-5); 8.59 (d, 1H, $J_{6,5}$=5.4, H-6); 8.62 (dd, 1H, $J_{2,5}$=1.5, $J_{2,4}$=0.9, H-2-furyl); 9.03 (s, 1H, H-2); 9.49 (d, 1H, $J_{8,5}$=1.0, H-8); $^{13}$C NMR (125.7 MHz, DMSO-d$_6$): 63.32 (CH$_2$-5'); 70.40 (CH-3'); 72.43 (CH-2'); 78.91 (CH-4'); 86.15 (CH-1'); 109.84 (C-4a); 110.67 (CH-4-furyl); 116.47 (CH-5); 124.23 (C-3-furyl); 124.98 (C-4b); 128.63, 128.82 (C-i-Bz); 128.89, 128.91, 128.97 (CH-m-Bz); 129.34 (C-i-Bz); 129.36, 129.50, 129.63 (CH-o-Bz); 133.73, 134.09 (CH-p-Bz); 134.16 (C-8a); 134.76 (CH-8); 142.37 (CH-6); 145.01 (CH-5-furyl); 145.34 (CH-2-furyl); 155.16 (C-4); 155.69 (C-9a); 156.16 (CH-2); 164.82, 165.02, 165.58 (CO-Bz); HR-ESI-MS: m/z (%): 681.1981 (100, [M+H]$^+$, calcd for C$_{39}$H$_{29}$O$_8$N$_4^+$: 681.1979); HR-ESI-MS: m/z (%): 703.1800 (100, [M+Na]$^+$, calcd for C$_{39}$H$_{28}$O$_8$N$_4$Na$^+$: 703.1799).

Example 32

4-(Furan-3-yl)-9-(β-n-ribofuranosyl)-9H-pyrido[2',3':4,5]pyrrolo[2,3-d]pyrimidine (1g)

To a suspension of nucleoside 15g (283 mg, 0.42 mmol) in MeOH (13 mL) was added sodium methoxide (30 μL, 25 wt. % in methanol, 0.13 mmol). The reaction mixture was stirred for 16 h at 70° C.

Then the solvent was evaporated and the product was crystallized from MeOH. Nucleoside 1g (120 mg, 78%) was obtained as a white solid.

$R_f$=0.25 (SiO$_2$; EtOAc); $[α]_D^{20}$=−18.1 (c=0.182 in DMSO); $^1$H NMR (500.0 MHz, DMSO-d$_6$): 3.68-3.78 (m, 2H, H-5'); 4.03 (td, 1H, $J_{4',5}$=3.5, $J_{4',3}$=2.5, H-4'); 4.24 (dd, 1H, $J_{3',2'}$=5.6, $J_{3',4'}$=2.5, H-3'); 4.73 (dd, 1H, $J_{2',1'}$=7.5, $J_{2',3'}$=5.6, H-2'); 5.20-5.34 (bm, 3H, OH-2',3',5'); 6.62 (d, 1H, $J_{1',2'}$=7.5, H-1'); 7.62 (dd, 1H, $J_{7,8}$=8.4, $J_{7,6}$=4.7, H-7); 7.68 (dd, 1H, $J_{4,5}$=1.9, $J_{4,3}$=0.8, H-4-furyl); 7.94 (dd, 1H, $J_{5,4}$=1.9, $J_{5,2}$=1.6, H-5-furyl); 8.62 (dd, 1H, $J_{8,7}$=8.4, $J_{8,6}$=1.4, H-8); 8.80 (dd, 1H, $J_{6,7}$=4.7, $J_{6,8}$=1.4, H-6); 9.08 (s, 1H, H-2); 10.05 (dd, 1H, $J_{2,5}$=1.6, $J_{2,4}$=0.8, H-2-furyl); $^{13}$C NMR (125.7 MHz, DMSO-d$_6$): 61.72 (CH$_2$-5'); 70.28 (CH-3'); 71.02 (CH-2'); 85.86 (CH-4'); 86.79 (CH-1'); 108.49 (C-4a); 110.49 (CH-4-furyl); 120.95 (CH-8); 121.91 (CH-7); 125.42 (C-3-furyl); 131.91 (C-8a); 138.28 (C-4b); 143.98 (CH-6); 144.21 (CH-5-furyl); 149.40 (CH-2-furyl); 152.52 (C-4); 155.47 (CH-2); 156.48 (C-9a); HR-ESI-MS: m/z (%): 391.1013 (100, [M+Na]$^+$, calcd for C$_{18}$H$_{16}$O$_5$N$_4$Na$^+$: 391.1012).

Example 33

4-(Furan-3-yl)-9-(β-D-ribofuranosyl)-9H-pyrido[4',3':4,5]pyrrolo[2,3-d]pyrimidine (2g)

Compound 2g was prepared as described for compound 1g from protected nucleoside 16g (396 mg, 0.58 mmol). The reaction mixture was stirred for 16 h at 22° C., and then the solvent was evaporated and the crude material was purified using reverse phase column chromatography (C-18, water/MeOH 0→60%). Nucleoside 2g (192 mg, 90%) was obtained as a white solid.

$R_f$=0.20 (SiO$_2$; CHCl$_3$/MeOH 10:1); $[α]_D^{20}$=−31.9 (c=0.254 in DMSO); NMR (500.0 MHz, DMSO-d$_6$): 3.73, 3.76 (2×ddd, 2×1H, $J_{gem}$=11.9, $J_{5',OH}$=5.1, $J_{5',4'}$=3.3, H-5'); 4.04 (td, 1H, $J_{4',5}$=3.3, $J_{4',3}$=2.7, H-4'); 4.26 (ddd, 1H, $J_{3',2'}$=5.8, $J_{3',OH}$=4.6, $J_{3',4'}$=2.7, H-3'); 4.74 (dd, 1H, $J_{2',1'}$=7.7, $J_{2',OH}$=6.4, $J_{2',3'}$=5.8, H-2'); 5.25 (d, 1H, $J_{OH,3'}$=4.6, OH-3'); 5.28 (t, 1H, $J_{OH,5'}$=5.1, OH-5'); 5.31 (d, 1H, $J_{OH,2'}$=6.4, OH-2'); 6.62 (d, 1H, $J_{1',2'}$=7.7, H-1'); 7.17 (dd, 1H, $J_{4,5}$=1.9, $J_{4,2}$=0.9, H-4-furyl); 8.03 (dd, 1H, $J_{5,4}$=1.9, $J_{5,2}$=1.5, H-5-furyl); 8.15 (dd, 1H, $J_{5,6}$=5.4, $J_{5,8}$=1.1, H-5); 8.56 (d, 1H, $J_{6,5}$=5.4, H-6); 8.61 (dd, 1H, $J_{2,5}$=1.5, $J_{2,4}$=0.9, H-2-furyl); 9.11 (s, 1H, H-2); 9.53 (d, 1H, $J_{8,5}$=1.0, H-8); $^{13}$C NMR (125.7 MHz, DMSO-d$_6$): 61.64 (CH$_2$-5'); 70.18 (CH-3'); 71.25 (CH-2'); 85.97 (CH-4'); 86.74 (CH-1'); 109.30 (C-4a); 110.72 (CH-4-furyl); 116.31 (CH-5); 124.34 (C-3-furyl); 125.12 (C-4b); 133.65 (C-8a); 136.41 (CH-8); 141.74 (CH-6); 144.97 (CH-5-furyl); 145.16 (CH-2-furyl); 154.84 (C-4); 156.25 (CH-2); 156.35 (C-9a); HR-ESI-MS: m/z (%): 369.1194 (100, [M+H]$^+$, calcd for C$_{18}$H$_{17}$O$_5$N$_4^+$: 369.1193); HR-ESI-MS: m/z (%): 391.1013 (100, [M+Na]$^+$, calcd for C$_{18}$H$_{16}$O$_5$N$_4$Na$^+$: 391.1012).

Example 34

4-(Thiophen-3-yl)-9-(2,3,5-tri-O-benzoyl-β-D-ribofuranosyl)-9H-pyrido[2',3':4,5]pyrrolo[2,3-d]pyrimidine (15h)

Protected nucleoside 13 (150 mg, 0.23 mmol), thiophen-3-ylboronic acid (25 mg, 0.35 mmol), K$_2$CO$_3$ (64 mg, 0.46 mmol) and Pd(PPh$_3$)$_4$ (13 mg, 0.01 mmol) were dissolved in toluene (5 mL) and heated to 100° C. for 22 h. Then, the reaction mixture was diluted with saturated solution of NaHCO$_3$ and extracted with EtOAc. Organic layer was dried over Na$_2$SO$_4$. After evaporation of solvent, the crude product was purified by column chromatography (SiO$_2$, petroleum ether/EtOAc 0→100%). Protected nucleoside 15h (112 mg, 70%) was obtained as a white solid.

$R_f$=0.54 (SiO$_2$; petroleum ether/EtOAc 2:1); $^1$H NMR (500.0 MHz, DMSO-d$_6$): 4.73 (dd, 1H, $J_{gem}$=12.3, $J_{5'b,4'}$=4.4, H-5'b); 4.86 (dd, 1H, $J_{gem}$=12.3, $J_{5'a,4'}$=3.2, H-5'b); 4.92 (ddd, 1H, =6.6, $J_{4',5}$=4.4, 3.2, H-4'); 6.40 (t, 1H, $J_{3',2'}$=$J_{3',4'}$=6.6, H-3'); 6.60 (dd, 1H, $J_{2',3}$=6.6, $J_{2',1'}$=4.7, H-2'); 7.09 (d, 1H, $J_{1',2'}$=4.7, H-1'); 7.41, 7.49, 7.50 (3×m, 3×2H, H-m-Bz); 7.55 (dd, 1H, $J_{7,8}$=8.4, $J_{7,6}$=4.7, H-7); 7.61, 7.65, 7.68 (3×m, 3×1H, H-p-Bz); 7.74 (dd, 1H, $J_{5,4}$=5.1, $J_{5,2}$=3.0, H-5-thienyl); 7.83, 7.95, 8.00 (3×m, 3×2H, H-o-Bz); 8.46 (dd, 1H, $J_{4,5}$=5.1, $J_{4,2}$=1.3, H-4-thienyl); 8.53 (dd, 1H, $J_{8,7}$=8.4, $J_{8,6}$=1.4, H-8); 8.78 (dd, 1H, $J_{6,7}$=4.7, $J_{6,8}$=1.4, H-6); 9.02 (s, 1H, H-2); 10.20 (dd, 1H, $J_{2,5}$=3.0, $J_{2,4}$=1.3, H-2-thienyl); $^{13}$C NMR (125.7 MHz, DMSO-d$_6$): 63.32 (CH$_2$-5'); 70.40 (CH-3'); 72.51 (CH-2'); 78.85 (CH-4'); 86.10 (CH-1'); 109.06 (C-4a); 119.48 (CH-8); 122.40 (CH-7); 122.40 (CH-5-thienyl); 128.66, 128.86 (C-i-Bz); 128.94, 128.99, 129.02 (CH-m-Bz); 129.11 (CH-4-thienyl); 129.42 (C-i-Bz); 129.42, 129.53, 129.66 (CH-o-Bz); 132.39 (C-8a); 133.66 (CH-2-thienyl); 133.82, 134.15 (CH-p-Bz); 138.10 (C-4b); 139.76 (C-3-thienyl); 144.25 (CH-6); 154.91 (C-4); 155.30 (CH-2); 156.30 (C-9a); 164.87, 165.07, 165.65 (CO-Bz); HR-ESI-MS: m/z (%): 697.1752 (100, [M+H]$^+$, calcd for C$_{39}$H$_{29}$O$_7$N$_4$S$^+$: 697.1751); HR-ESI-MS: m/z (%): 719.1572 (100, [M+Na]$^+$, calcd for C$_{39}$H$_{28}$O$_7$N$_4$NaS$^+$: 719.1570).

Example 35

4-(Thiophen-3-yl)-9-(2,3,5-tri-O-benzoyl-β-D-ribofuranosyl)-9H-pyrido[4',3':4,5]pyrrolo[2,3-d]pyrimidine (16h)

Protected nucleoside 14 (120 mg, 0.19 mmol), thiophen-3-ylboronic acid (41 mg, 0.57 mmol), K$_2$CO$_3$ (52 mg, 0.38 mmol) and Pd(PPh$_3$)$_4$ (12 mg, 0.01 mmol) were dissolved in toluene (4 mL) and heated to 100° C. for 24 h. Then, the reaction mixture was diluted with saturated solution of NaHCO$_3$ and extracted with EtOAc. Organic layer was dried over Na$_2$SO$_4$. After evaporation of solvent, the crude product was purified by column chromatography (SiO$_2$, petroleum ether/EtOAc 0→100%). Protected nucleoside 16h (73 mg, 57%) was obtained as a white solid.

R$_f$=0.51 (SiO$_2$; petroleum ether/EtOAc 1:2); $^1$H NMR (500.0 MHz, DMSO-d$_6$): 4.76 (dd, 1H, J$_{gem}$=12.3, J$_{5',4'}$=4.6, H-5'b); 4.85 (dd, 1H, J$_{gem}$=12.3, J$_{5'a,4'}$=3.2, H-5'a); 4.94 (ddd, 1H, J$_{4',3'}$=6.5, J$_{4',5'}$=4.6, 3.2, H-4'); 6.40 (t, 1H, J$_{3',2'}$=J$_{3',4'}$=6.5, H-3'); 6.66 (dd, 1H, J$_{2',3'}$=6.5, J$_{2',1'}$=4.7, H-2'); 7.16 (d, 1H, J$_{1',2'}$=4.7, H-1'); 7.42, 7.48, 7.51 (3×m, 3×2H, H-m-Bz); 7.62, 7.65, 7.69 (3×m, 3×1H, H-p-Bz); 7.72 (dd, 1H, J$_{4,5}$=5.0, J$_{4,3}$=1.3, H-4-thienyl); 7.85 (m, 2H, H-o-Bz); 7.88 (dd, 1H, J$_{5,4}$=5.0, J$_{5,2}$=2.9, H-5-thienyl); 7.95 (m, 2H, H-o-Bz); 8.00 8.03 (m, 3H, H-5, H-o-Bz); 8.41 (dd, 1H, J$_{2,5}$=2.9, J$_{2,4}$=1.3, H-2-thienyl); 8.56 (d, 1H, J$_{6,5}$=5.3, H-6); 9.05 (s, 1H, H-2); 9.49 (d, 1H, J$_{8,5}$=1.1, H-8); $^{13}$C NMR (125.7 MHz, DMSO-d$_6$): 63.33 (CH$_2$-5'); 70.39 (CH-3'); 72.45 (CH-2'); 78.91 (CH-4'); 86.15 (CH-1'); 109.87 (C-4a); 116.28 (CH-5); 125.11 (C-4b); 127.98 (CH-5-thienyl); 128.17 (CH-4-thienyl); 128.64, 128.82 (C-i-Bz); 128.89, 128.92, 128.97 (CH-m-Bz); 129.34 (C-i-Bz); 129.37, 129.50, 129.63 (CH-o-Bz); 129.69 (CH-2-thienyl); 133.74, 134.10 (CH-p-Bz); 134.26 (C-8a); 134.81 (CH-8); 138.84 (C-3-thienyl); 142.27 (CH-6); 155.83 (C-9a); 156.18 (CH-2); 157.42 (C-4); 164.83, 165.02, 165.58 (CO-Bz); HR-ESI-MS: m/z (%): 697.1753 (100, [M+H]$^+$, calcd for C$_{39}$H$_{29}$O$_7$N$_2$S$^+$: 697.1751); HR-ESI-MS: m/z (%): 719.1573 (100, [M+Na]$^+$, calcd for C$_{39}$H$_{28}$O$_7$N$_4$NaS$^+$: 719.1570).

Example 36

4-(Thiophen-3-yl)-9-(β-D-ribofuranosyl)-9H-pyrido[2',3':4,5]pyrrolo[2,3-d]pyrimidine (1h)

To a suspension of nucleoside 15h (160 mg, 0.23 mmol) in MeOH (7 mL) was added sodium methoxide (16 μL, 25 wt. % in MeOH, 0.07 mmol). The reaction mixture was stirred for 16 h at 50° C., and then the solvent was evaporated and the crude material was purified using column chromatography (SiO$_2$, CHCl$_3$/MeOH 0→10%). Nucleoside 1h (62 mg, 70%) was obtained as a white solid.

R$_f$=0.44 (SiO$_2$; EtOAc); [α]$_D^{20}$=−17.6 (c=0.199 in DMSO); $^1$H NMR (500.0 MHz, DMSO-d$_6$): 3.72 (ddd, 1H, J$_{gem}$=12.0, J$_{5'b,OH}$=5.2, J$_{5'b,4'}$=3.3, H-5'b); 3.75 (ddd, 1H, J$_{gem}$=12.0, J$_{5'a,OH}$=5.2, J$_{5'a,4'}$=3.3, H-5'b); 4.03 (td, 1H, J$_{4',5'}$=3.3, J$_{4',3'}$=2.9, H-4'); 4.25 (ddd, 1H, J$_{3',2'}$=6.2, J$_{3',OH}$=4.2, J$_{3',4'}$=2.9, H-3'); 4.73 (dt, 1H, J$_{2',1'}$=7.5, J$_{2',3'}$=J$_{2',OH}$=5.4, H-2'); 5.23 (d, 1H, J$_{OH,3'}$=4.2, OH-3'); 5.28 (t, 1H, J$_{OH,5'}$=5.2, OH-5'); 5.31 (d, 1H, J$_{OH,2'}$=5.4, OH-2'); 6.65 (d, 1H, J$_{1',2'}$=7.5, H-1'); 7.64 (dd, 1H, J$_{7,8}$=8.4, J$_{7,6}$=4.7, H-7); 7.75 (dd, 1H, J$_{5,4}$=5.1, J$_{5,2}$=3.0, H-5-thienyl); 8.48 (dd, 1H, J$_{4,5}$=5.1, J$_{4,2}$=1.2, H-4-thienyl); 8.64 (dd, 1H, J$_{8,7}$=8.4, J$_{8,6}$=1.4, H-8); 8.78 (dd, 1H, J$_{6,7}$=4.7, J$_{6,8}$=1.4, H-6); 9.10 (s, 1H, H-2); 10.25 (dd, 1H, J$_{2,5}$=3.0, J$_{2,4}$=1.2, H-2-thienyl); $^{13}$C NMR (125.7 MHz, DMSO-d$_6$): 61.71 (CH$_2$-5'); 70.26 (CH-3'); 70.98 (CH-2'); 85.85 (CH-4'); 86.77 (CH-1'); 108.52 (C-4a); 121.00 (CH-8); 122.14 (CH-7); 126.13 (CH-5-thienyl); 129.13 (CH-4-thienyl); 131.88 (C-8a); 133.39 (CH-2-thienyl); 138.26 (C-4b); 139.93 (C-3-thienyl); 143.71 (CH-6); 154.61 (C-4); 155.27 (CH-2); 156.87 (C-9a); HR-ESI-MS: m/z (%): 385.0956 (100, [M+H]$^+$, calcd for C$_{18}$H$_{17}$O$_4$N$_4$S$^+$: 385.0965); HR-ESI-MS: m/z (%): 407.0786 (100, [M+Na]$^+$, calcd for C$_{18}$H$_{16}$O$_4$NaS$^+$: 407.0784).

Example 37

4-(Thiophen-3-yl)-9-(β-D-ribofuranosyl)-9H-pyrido[4',3':4,5]pyrrolo[2,3-d]pyrimidine (2h)

Nucleoside 2h was prepared as described for compound 1h, from protected nucleoside 16h (268 mg, 0.39 mmol). The reaction mixture was stirred for 16 h at 60° C., and then solvent was evaporated and crude material was purified using column chromatography (SiO$_2$, CHCl$_3$/MeOH 0→10%). Nucleoside 2h (106 mg, 72%) was obtained as a white solid.

R$_f$=0.20 (SiO$_2$; CHCl$_3$/MeOH 10:1); [α]$_D^{20}$=−32.5 (c=0.283 in DMSO); $^1$H NMR (600.1 MHz, DMSO-d$_6$): 3.73 (ddd, 1H, J$_{gem}$=11.9, J$_{5'b,OH}$=5.1, J$_{5'b,4'}$=3.5, H-5'b); 3.76 (ddd, 1H, J$_{gem}$=11.9, J$_{5'a,OH}$=5.1, J$_{5'a,4'}$=3.2, H-5'a); 4.05 (ddd, 1H, J$_{4',5'}$=3.5, 3.2, J$_{4',3'}$=2.7, H-4'); 4.26 (ddd, 1H, J$_{3',2'}$=5.8, J$_{3',OH}$=4.6, J$_{3',4'}$=2.7, H-3'); 4.76 (ddd, 1H, J$_{2',1'}$=7.6, J$_{2',OH}$=6.4, J$_{2',3'}$=5.8, H-2'); 5.25 (d, 1H, J$_{OH,3'}$=4.6, OH-3'); 5.27 (t, 1H, J$_{OH,5'}$=5.1, OH-5'); 5.31 (d, 1H, J$_{OH,2'}$=6.4, OH-2'); 6.64 (d, 1H, J$_{1',2'}$=7.6, H-1'); 7.73 (dd, 1H, J$_{4,5}$=5.0, J$_{4,2}$=1.3, H-4-thienyl); 7.88 (dd, 1H, J$_{5,4}$=5.0, J$_{5,2}$=2.9, H-5-thienyl); 8.01 (dd, 1H, J$_{5,6}$=5.3, J$_{5,8}$=1.1, H-5); 8.39 (dd, 1H, J$_{2,5}$=2.9, J$_{2,4}$=1.3, H-2-thienyl); 8.53 (d, 1H, J$_{6,5}$=5.3, H-6); 9.13 (s, 1H, H-2); 9.53 (d, 1H, J$_{8,5}$=1.1, H-8); $^{13}$C NMR (150.9 MHz, DMSO-d$_6$): 61.64 (CH$_2$-5'); 70.18 (CH-3'); 71.25 (CH-2'); 85.97 (CH-4'); 86.76 (CH-1'); 109.30 (C-4a); 116.11 (CH-5); 125.24 (C-4b); 127.93 (CH-5-thienyl); 128.19 (CH-4-thienyl); 129.40 (CH-2-thienyl); 133.74 (C-8a); 136.45 (CH-8); 139.02 (C-3-thienyl); 141.62 (CH-6); 156.24 (CH-2); 156.47 (C-9a); 157.15 (C-4); HR-ESI-MS: m/z (%): 385.0965 (100, [M+H]$^+$, calcd for C$_{18}$H$_{17}$O$_4$N$_4$S$^+$: 385.0965).

Example 38

4-(Benzofuran-2-yl)-9-(2,3,5-tri-O-benzoyl-β-D-ribofuranosyl)-9H-pyrido[2',3':4,5]pyrrolo[2,3-d]pyrimidine (15i)

Protected nucleoside 13 (100 mg, 0.15 mmol), benzofuran-2-ylboronic acid (38 mg, 0.23 mmol), K$_2$CO$_3$ (43 mg, 0.3 mmol), Pd(PPh$_3$)$_2$Cl$_2$ (11 mg, 0.01 mmol) and Et$_3$N (33 μl, 0.23 mmol) were dissolved in toluene (4 mL) and heated to 100° C. for 24 h. Then, the solvent was evaporated and the crude material was purified by column chromatography (SiO$_2$, petroleum ether/DCM/EtOAc 1:1:0→1:1:2). Protected nucleoside 15i (63 mg, 56%) was obtained as a yellowish solid.

R$_f$=0.52 (SiO$_2$; petroleum ether/DCM/EtOAc 4:1:1); $^1$H NMR (500.0 MHz, DMSO-d$_6$): 4.74 (dd, 1H, J$_{gem}$=12.3, J$_{5'b,4'}$=4.4, H-5'b); 4.88 (dd, 1H, J$_{gem}$=12.3, J$_{5'a,4'}$=3.2, H-5'b); 4.93 (ddd, 1H, J$_{4',3'}$=6.7, J$_{4',5'}$=4.4, 3.2, H-4'); 6.43 (t, 1H, J$_{3',2'}$=J$_{3',4'}$=6.7, H-3'); 6.61 (dd, 1H, J$_{2',3'}$=6.7, J$_{2',1'}$=4.6, H-2'); 7.12 (d, 1H, J$_{1',2'}$=4.6, H-1'); 7.39 (ddd, 1H, J$_{5,4}$=8.0, J$_{5,6}$=7.2, J$_{5,7}$=1.0, H-5-benzofuryl); 7.42, 7.50, 7.51 (3×m, 3×2H, H-m-Bz); 7.53 (ddd, 1H, J$_{6,7}$=8.4, J$_{6,5}$=7.2, J$_{6,4}$=1.3, H-6-benzofuryl); 7.60-7.71 (m, 4H, H-7, H-p-Bz); 7.80 (dq, 1H, J$_{7,6}$=8.4, J$_{7,3}$=J$_{7,4}$=J$_{7,5}$=1.0, H-7-benzofuryl); 7.83 (m, 2H, H-o-Bz); 7.95-7.98 (m, 3H, H-4-benzofuryl, H-o-Bz); 8.01 (m, 2H, H-o-Bz); 8.58 (dd, 1H, J$_{8,7}$=8.5, J$_{8,6}$=1.4, H-8); 8.90 (dd, 1H, J$_{6,7}$=4.7, J$_{6,8}$=1.4, H-6); 9.11 (s, 1H, H-2); 9.91 (d, 1H, J$_{3,7}$=1.0, H-3-benzofuryl); $^{13}$C NMR (125.7 MHz, DMSO-d$_6$): 63.23 (CH$_2$-5'); 70.33 (CH-3'); 72.62 (CH-2'); 78.85 (CH-4'); 86.12 (CH-1'); 108.57 (C-4a); 111.99 (CH-7-benzofuryl); 115.96 (CH-3-benzofuryl); 119.58 (CH-8); 122.64 (CH-7); 123.22 (CH-4-benzofuryl); 123.90 (CH-5- benzofuryl); 127.62 (CH-6-benzofuryl); 128.24 (C-3a-benzofuryl); 128.66, 128.83 (C-i-Bz); 128.89, 128.95, 128.97 (CH-m-Bz); 129.38 (CH-o-Bz); 129.39 (C-i-Bz); 129.50, 129.62 (CH-o-Bz); 132.79 (C-8a); 133.76, 134.10 (CH-p-Bz); 137.43 (C-4b); 144.65 (CH-6); 149.21 (C-4); 151.93 (C-2-benzofuryl); 155.12 (C-7a-benzofuryl); 155.24 (CH-2); 155.89 (C-9a); 164.84, 165.02, 165.58 (CO-Bz); HR-ESI-MS: m/z (%): 731.2139 (100, [M+]$^+$, calcd for $C_{43}H_{31}O_8N_4^+$: 731.2136); HR-ESI-MS: m/z (%): 753.1958 (100, [M+Na]$^+$, calcd for $C_{43}H_{30}O_8N_4Na^+$: 753.1955).

Example 39

4-(Benzofuran-2-yl)-9-(2,3,5-tri-O-benzoyl-β-D-ribofuranosyl)-9H-pyrido[4',3':4,5]pyrrolo[2,3-d]pyrimidine (16i)

Protected nucleoside 14 (400 mg, 0.62 mmol), benzofuran-2-ylboronic acid (301 mg, 1.86 mmol), $K_2CO_3$ (171 mg, 1.24 mmol) and Pd(PPh$_3$)$_4$ (71 mg, 0.06 mmol) were dissolved in toluene (16 mL) and heated to 100° C. for 18 h. Then, the solvent was evaporated and the crude product was purified by column chromatography (SiO$_2$, cyclohexane/EtOAc 0→100%). Protected nucleoside 16i (288 mg, 64%) was obtained as a white solid.

$R_f$=0.50 (SiO$_2$; cyclohexane/EtOAc 1:1); $^1$H NMR (500.0 MHz, DMSO-d$_6$): 4.76 (dd, 1H, $J_{gem}$=12.3, $J_{5'b,4'}$=4.7, H-5'b); 4.86 (dd, 1H, $J_{gem}$=12.3, $J_{5'a,4'}$=3.2, H-5'a); 4.95 (ddd, 1H, $J_{4',3'}$=6.6, $J_{4',5'}$4.7, 3.2, H-4'); 6.40 (t, 1H, $J_{3',2'}$=$J_{3',4'}$=6.6, H-3'); 6.64 (dd, 1H, $J_{2',3'}$=6.6, $J_{2',1'}$=4.6, H-2'); 7.19 (d, 1H, $J_{1',2'}$=4.6, H-1'); 7.40-7.53 (m, 7H, H-5-benzofuryl, H-m-Bz); 7.58 (ddd, 1H, $J_{6,7}$=8.4, $J_{6,5}$=7.2, $J_{6,4}$=1.3, H-6-benzofuryl); 7.62, 7.63, 7.69 (3×m, 3×1H, H-p-Bz); 7.85 (m, 2H, H-o-Bz); 7.90 (ddd, 1H, $J_{4,5}$=7.8, $J_{4,6}$=1.3, $J_{4,7}$=1.0, H-4-benzofuryl); 7.94, 8.02 (2×m, 2×2H, H-o-Bz); 8.07 (dq, 1H, $J_{7,6}$=8.4, $J_{7,3}$=$J_{7,4}$=$J_{7,5}$=1.0, H-7-benzofuryl); 8.11 (d, 1H, $J_{3,7}$=1.0, H-3-benzofuryl); 8.75 (d, 1H, $J_{6,5}$=5.4, H-6); 8.93 (dd, 1H, $J_{5,6}$=5.4, $J_{5,8}$=1.0, H-5); 9.09 (s, 1H, H-2); 9.52 (d, 1H, $J_{8,5}$=1.0, H-8); $^{13}$C NMR (125.7 MHz, DMSO-d$_6$): 63.36 (CH$_2$-5'); 70.40 (CH-3'); 72.50 (CH-2'); 78.95 (CH-4'); 86.18 (CH-1'); 108.22 (C-4a); 111.80 (CH-3-benzofuryl); 112.36 (CH-7-benzofuryl); 118.85 (CH-5); 123.07 (CH-4-benzofuryl); 124.48 (CH-5-benzofuryl); 124.91 (C-4b); 127.48 (CH-6-benzofuryl); 127.55 (C-3a-benzofuryl); 128.67, 128.84 (C-i-Bz); 128.91, 128.92, 128.99 (CH-m-Bz); 129.34 (C-i-Bz); 129.37, 129.52, 129.65 (CH-o-Ph); 133.73, 134.11, 134.12 (CH-p-Bz); 134.67 (C-8a); 134.76 (CH-8); 142.98 (CH-6); 150.07 (C-4); 153.32 (C-2-benzofuryl); 155.79 (C-7a-benzofuryl); 155.94 (CH-2); 156.43 (C-9a); 164.85, 165.03, 165.60 (CO-Bz); HR-ESI-MS: m/z (%): 731.2139 (100, [M+H]$^+$, calcd for $C_{43}H_{31}O_8N_4^+$: 731.2136).

Example 40

4-(Benzofuran-2-yl)-9-(β-D-ribofuranosyl)-9H-pyrido[2',3':4,5]pyrrolo[2,3-d]pyrimidine (1i)

To a suspension of nucleoside 15i (180 mg, 0.25 mmol) in MeOH (8 mL) was added sodium methoxide (17 μL, 25 wt. % in MeOH, 0.08 mmol). The reaction mixture was stirred 16 h at 70° C. Then the solvent was evaporated and the product was crystallized from MeOH. Nucleoside 1i (71 mg, 69%) was obtained as a yellowish solid.

$R_f$=0.48 (SiO$_2$; CHCl$_3$/MeOH 10:1); $[α]_D^{20}$=−27.7 (c=0.271 in DMSO); $^1$H NMR (500.0 MHz, DMSO-d$_6$): 3.72 (ddd, 1H, $J_{gem}$=11.9, $J_{5'b,OH}$=5.2, $J_{5'b,4'}$=3.6, H-5'b); 3.77 (ddd, 1H, $J_{gem}$=11.9, $J_{5'a,OH}$=5.2, $J_{5'a,4'}$=3.2, H-5'b); 4.05 (ddd, 1H, $J_{4',5'}$=3.6, 3.2 $J_{4',3'}$=2.7, H-4'); 4.26 (ddd, 1H, $J_{3',2'}$=5.6, $J_{3',OH}$=4.5, $J_{3',4'}$=2.7, H-3'); 4.74 (ddd, 1H, $J_{2',1'}$=7.5, $J_{2',OH}$=6.2, $J_{2',3'}$=5.6, H-2'); 5.25 (d, 1H, $J_{OH,3'}$=4.5, OH-3'); 5.30 (t, 1H, $J_{OH,5'}$=5.2, 5.0, OH-5'); 5.33 (d, 1H, $J_{OH,2'}$=6.2, OH-2'); 6.68 (d, 1H, $J_{1',2'}$=7.5, H-1'); 7.39 (ddd, 1H, $J_{5,4}$=8.0, $J_{5,6}$=7.2, $J_{5,7}$=1.0, H-5-benzofuryl); 7.53 (ddd, 1H, $J_{6,7}$=8.4, $J_{6,5}$=7.2, $J_{6,4}$=1.3, H-6-benzofuryl); 7.63 (dd, 1H, $J_{7,8}$=8.4, $J_{7,6}$=4.7, H-7); 7.80 (dq, 1H, $J_{7,6}$=8.4, $J_{7,3}$=$J_{7,4}$=$J_{7,5}$=1.0, H-7-benzofuryl); 7.96 (ddd, 1H, $J_{4,5}$=8.0, $J_{4,6}$=1.3, $J_{4,7}$=1.0, H-4-benzofuryl); 8.69 (dd, 1H, $J_{8,7}$=8.4, $J_{8,6}$=1.4, H-8); 8.89 (dd, 1H, $J_{6,7}$=4.7, $J_{6,8}$=1.4, H-6); 9.19 (s, 1H, H-2); 9.94 (d, 1H, $J_{3,7}$=1.0, H-3-benzofuryl); $^{13}$C NMR (125.7 MHz, DMSO-d$_6$): 61.71 (CH$_2$-5'); 70.29 (CH-3'); 71.10 (CH-2'); 85.95 (CH-4'); 86.82 (CH-1'); 108.57 (C-4a); 111.98 (CH-7-benzofuryl); 115.73 (CH-3-benzofuryl); 121.20 (CH-8); 122.44 (CH-7); 123.18 (CH-4-benzofuryl); 123.89 (CH-5-benzofuryl); 127.53 (CH-6-benzofuryl); 128.29 (C-3a-benzofuryl); 132.27 (C-8a); 137.65 (C-4b); 144.20 (CH-6); 148.97 (C-4); 152.12 (C-2-benzofuryl); 155.09 (C-7a-benzofuryl); 155.29 (CH-2); 156.54 (C-9a); HR-ESI-MS: m/z (%): 419.1350 (100, [M+H]$^+$, calcd for $C_{22}H_{19}O_5N_4^+$: 419.1350); HR-ESI-MS: m/z (%): 441.1170 (100, [M+Na]$^+$, calcd for $C_{22}H_{18}O_5N_4Na^+$: 441.1169).

Example 41

4-(Benzofuran-2-yl)-9-(β-D-ribofuranosyl)-9H-pyrido[4',3':4,5]pyrrolo[2,3-d]pyrimidine (2i)

To a suspension of nucleoside 16i (249 mg, 0.25 mmol) in MeOH (10 mL) was added sodium methoxide (23 μL, 25 wt. % in MeOH, 0.10 mmol). The reaction mixture was stirred for 16 h at 60° C. Then the solvent was evaporated and the crude material was purified using column chromatography (SiO$_2$, CHCl$_3$/MeOH 0→10%). Nucleoside 2i (112 mg, 79%) was obtained as a yellowish solid.

$R_f$=0.26 (SiO$_2$; CHCl$_3$/MeOH 10:1); $[α]_D^{20}$=−50.5 (c=0.263 in DMSO); $^1$H NMR (500.0 MHz, DMSO-d$_6$): 3.75 (ddd, 1H, $J_{gem}$=11.9, $J_{5'b,OH}$=5.0, $J_{5'b,4'}$=3.5, H-5'b); 3.78 (ddd, 1H, $J_{gem}$=11.9, $J_{5'a,OH}$=5.0, $J_{5'a,4'}$=3.2, H-5'a); 4.06 (ddd, 1H, $J_{4',5'}$=3.5, 3.2, $J_{4',3'}$=2.8, H-4'); 4.28 (ddd, 1H, $J_{3',2'}$=5.7, $J_{3',OH}$=4.7, $J_{3',4'}$=2.8, H-3'); 4.77 (ddd, 1H, $J_{2',1'}$=7.6, $J_{2'OH}$=6.3, $J_{2',3'}$=5.7, H-2'); 5.26 (d, 1H, $J_{OH,3'}$=4.6, OH-3'); 5.29 (t, 1H, $J_{OH,5'}$=5.0, OH-5'); 5.33 (d, 1H, $J_{OH,2'}$=6.3, OH-2'); 6.68 (d, 1H, $J_{1',2'}$=7.6, H-1'); 7.44 (ddd, 1H, $J_{5,4}$=7.8, $J_{5,6}$=7.2, $J_{5,7}$=1.0, H-5-benzofuryl); 7.58 (ddd, 1H, $J_{6,7}$=8.4, $J_{6,5}$=7.2, $J_{6,4}$=1.3, H-6-benzofuryl); 7.90 (ddd, 1H, $J_{4,5}$=7.8, $J_{4,6}$=1.3, $J_{4,7}$=1.0, H-4-benzofuryl); 8.05 (dq, 1H, $J_{7,6}$=8.4, $J_{7,3}$=$J_{7,4}$=$J_{7,5}$=1.0, H-7-benzofuryl); 8.09 (d, 1H, $J_{3,7}$=1.0, H-3-benzofuryl); 8.72 (d, 1H, $J_{6,5}$=5.4, H-6); 8.93 (dd, 1H, $J_{5,6}$=5.4, $J_{5,8}$=1.1, H-5); 9.16 (s, 1H, H-2); 9.57 (d, 1H, $J_{8,5}$=1.1, H-8); $^{13}$C NMR (125.7 MHz, DMSO-d$_6$): 61.61 (CH$_2$-5'); 70.12 (CH-3'); 71.17 (CH-2'); 85.97 (CH-4'); 86.80 (CH-1'); 107.70 (C-4a); 111.51 (CH-3-benzofuryl); 112.30 (CH-7-benzofuryl); 118.64 (CH-5); 123.00 (CH-4-benzofuryl); 124.43 (CH-5-benzofuryl); 125.00 (C-4b); 127.34 (CH-6-benzofuryl); 127.57 (C-3a-benzofuryl); 134.16 (C-8a); 136.38 (CH-8); 142.31 (CH-6); 149.79 (C-4); 153.49 (C-2-benzofuryl); 155.71 (C-7a-benzofuryl); 156.02 (CH-2); 157.07 (C-9a); HR-ESI-MS: m/z (%): 419.1350 (100, [M+H]$^+$, calcd for $C_{22}H_{19}O_5N_4^+$: 419.1350).

In Vitro Antitumor Activity

To evaluate the antitumor activity of newly prepared compounds for in vitro conditions, we used cytotoxic MTS test (Nosková V. et al., Neoplasma 2002, 49, 418-425) on cell lines derived from normal tissues or tumors. Specifically, cell lines K562 (human acute myeloid leukemia); K562-Tax (human acute myeloid leukemia, paclitaxel resistant subline, overexpress multiple drug resistant protein PgP); CEM (T-lymfoblastic leukemia); CEM-DNR-bulk (T-lymfoblastic leukemia, doxorubicin resistant); A549 (human lung adenocarcinoma); HCT116p53 wt (human colorectal cancer, wild-type); HCT116p53−/−(human colorectal cancer, mutant p53) a U2OS (human bone osteosarcoma) were used. Express characteristics, susceptibility profiles of classic antitumor drugs as well as methodology of cytotoxic MTS test have been repeatedly published (Denizot, F.; Lang, R., *J. Immunol. Meth.* 1986, 89, 271-277; Noskova, V., see above; Šarek J. et al., *J. Med. Chem.*, 2003, 46, 5402-5415).

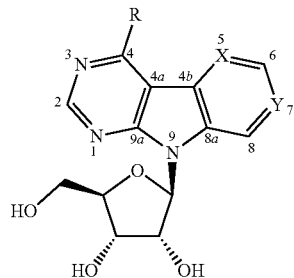

wherein
X is a nitrogen atom and Y is a carbon atom; or
X is a carbon atom and Y is a nitrogen atom;
and wherein
R is selected from the group consisting of

TABLE 4

Cytotoxic activities of prepared compounds

| Sloučenina | A549 | BJ | CCRF-CEM | CEM-DNR | HCT116 | HCT116p53 | K562 | K562-TAX | MRC-5 | U2OS | Hep G2 | HL 60 | CEM | HeLa |
|---|---|---|---|---|---|---|---|---|---|---|---|---|---|---|
| 1a | E | E | E | E | E | E | E | E | E | E | E | E | E | E |
| 1b | E | E | E | E | E | E | E | E | E | E | E | E | E | E |
| 1c | E | B | A | E | D | D | D | E | E | B | B | A | E | E |
| 1d | E | E | A | E | E | E | C | E | E | B | E | E | E | E |
| 1e | E | E | E | E | E | E | E | E | E | E | E | E | E | E |
| 1f | E | E | E | E | E | E | E | E | E | E | E | E | E | E |
| 1g | E | E | E | E | E | E | E | E | E | E | E | E | E | E |
| 1h | E | E | E | E | E | E | E | E | E | E | E | E | E | E |
| 1i | E | E | C | E | E | E | E | E | E | E | E | E | E | E |
| 2a | E | E | A | B | B | B | B | B | E | B | B | A | B | B |
| 2b | C | E | A | B | A | A | A | B | E | A | B | A | A | B |
| 2c | B | B | A | B | A | A | A | B | E | A | A | A | A | B |
| 2d | E | B | A | B | B | B | B | B | E | B | B | A | A | B |
| 2e | E | E | E | E | E | E | E | E | E | E | E | E | E | E |
| 2f | E | E | E | E | E | E | E | E | E | E | E | E | E | E |
| 2g | E | E | E | E | E | E | E | E | E | E | E | E | E | E |
| 2h | E | E | E | E | E | E | E | E | E | E | E | E | E | E |
| 2i | C | D | B | C | B | C | C | C | C | C | E | E | E | E |

IC50: A = 0.2-0.9 μmol · l$^{-1}$;
B = 0.9-10 μmol · l$^{-1}$;
C = 10-25 μmol · l$^{-1}$;
D = 25-50 μmol · l$^{-1}$;
E > 50 μmol · l$^{-1}$ If tested compounds showed activity in in vitro cytotoxic test (Table 4); it was selective against broad spectrum of cancer cell lines of various histogenetic origin (mesenchymal or epitelial tumors) with significantly lower activity against normal human fibroblasts (MRC-5 cell line) and therefore they showed promising in vitro therapeutic index (15-2500). Cytotoxic activity against cancer cells was independent on p53 gene status, same activities were found for HCT116 (p53 wild type) and for mutant line with deleted gene HCT116 (p53−/−).

INDUSTRIAL APPLICABILITY

The compounds in this patent are useful as pharmaceuticals or components of drugs effective against cancer and leukemia.

The invention claimed is:
1. Substituted pyridopyrrolopyrimidine ribonucleosides of general formula I:

C1-C5 alkyl, optionally substituted by at least one substitutent selected from hydroxy, sulfanyl, amino, C1-C5 alkoxy, C1-C5 sulfanyl, C1-C5 alkylamino, and di(C1-C5 alkyl)amino;
C2-C6 alkenyl, optionally substituted by at least one substitutent selected from hydroxy, sulfanyl, amino, C1-C5 alkoxy, C1-C5 sulfanyl, C1-C5 alkylamino, and di(C1-C5 alkyl)amino;
C6-C12 aryl, optionally substituted by at least one substitutent selected from C1-C5 alkyl, hydroxy, sulfanyl, amino, C1-C5 alkoxy, C1-C5 sulfanyl, C1-C5 alkylamino, and di(C1-C5 alkyl)amino;
C4-12 heteroaryl, comprising at least one heteroatom selected from O and S; optionally substituted by at least one substituent selected from C1-C5 alkyl, hydroxy, sulfanyl, amino, C1-C5 alkoxy, C1-C5 sulfanyl, C1-C5 alkylamino, and di(C1-C5 alkyl) amino;
amino,
C1-C5 alkylamino, di(C1-C5 alkyl)amino,
C1-C5 alkoxy, and
C1-C5 alkylsulfanyl,
and pharmaceutically acceptable salt thereof, their optical isomers and mixtures of such optical isomers, or racemic mixtures.

2. Substituted pyridopyrrolopyrimidine ribonucleosides of general formula I according to claim 1, where R is selected from the group consisting of amino, C1-C5 alkyl, phenyl, naphthyl, furan-2-yl, furan-3-yl, thiophen-2-yl, thiophen-3-yl, benzofuryl, C1-C5 alkylsulfanyl, C1-C5 alkylamino, di(C1-C5 alkyl)amino, and C1-C5 alkoxy group.

3. Substituted pyridopyrrolopyrimidine ribonucleosides of general formula I according to claim 1, where R is selected from the group consisting of amino, thiophen-3-yl, furan-2-yl, furan-3-yl, benzofuran-2-yl, methylsulfanyl, methoxy, dimethylamino, methyl and chloro.

4. Substituted pyridopyrrolopyrimidine ribonucleosides of general formula I according to claim 1, being selected from the following compounds:
- 4-methyl-9-(β-D-ribofuranosyl)-9H-pyrido[2',3':4,5]pyrrolo[2,3-d]pyrimidine
- 4-amino-9-(β-D-ribofuranosyl)-9H-pyrido[2',3':4,5]pyrrolo[2,3-d]pyrimidine
- 4-(benzofuran-2-yl)-9-(β-D-ribofuranosyl)-9H-pyrido[4',3':4,5]pyrrolo[2,3-d]pyrimidine
- 4-methyl-9-(β-D-ribofuranosyl)-9H-pyrido[4',3':4,5]pyrrolo[2,3-d]pyrimidine
- 4-amino-9-(β-D-ribofuranosyl)-9H-pyrido[4',3':4,5]pyrrolo[2,3-d]pyrimidine
- 4-methoxy-9-(β-D-ribofuranosyl)-9H-pyrido[4',3':4,5]pyrrolo[2,3-d]pyrimidine, and
- 4-(methylsulfanyl)-9-(β-D-ribofuranosyl)-9H-pyrido[4',3':4,5]pyrrolo[2,3-d]pyrimidine.

5. Method of inhibition of pathological cell proliferation of tumor or non-tumor origin, the method comprising the step of administering substituted pyridopyrrolopyrimidine ribonucleosides of general formula I according to claim 1 to a subject in need thereof.

6. Method of treatment of tumor or cancer diseases, the method comprising the step of administering substituted pyridopyrrolopyrimidine ribonucleosides of general formula I according to claim 1 to a subject in need thereof.

7. Method of treatment of non-tumor disease associated with cell hyperproliferation, the method comprising the step of administering substituted pyridopyrrolopyrimidine ribonucleosides of general formula I according to claim 1 to a subject in need thereof.

8. A pharmaceutical composition characterised in that it comprises a therapeutically effective amount of at least one compound of general formula I according to claim 1, and optionally also at least one pharmaceutically acceptable excipient.

9. Method of inhibition of pathological cell proliferation of tumor or non-tumor origin and/or of treatment of tumor or non tumor or cancer disease associated with cell hyperproliferation, the method comprising the step of administering the pharmaceutical composition according to claim 8 to a subject in need of such treatment.

10. Method of treatment of tumor or non-tumor or cancer disease associated with cell hyperproliferation, said method comprising the step of administering substituted pyridopyrrolopyrimidine ribonucleosides of general formula I according to claim 1 to a subject in need of such treatment.

11. Method of treatment of epithelial, mesenchymal or neuroectoderm origin tumors, said method comprising the step of administering substituted pyridopyrrolopyrimidine ribonucleosides of general formula I according to claim 1 to a subject in need of such treatment.

* * * * *